(12) United States Patent
Chen

(10) Patent No.: US 9,346,764 B2
(45) Date of Patent: May 24, 2016

(54) IMIDAZOLIDINEDIONE COMPOUNDS AND THEIR USES

(71) Applicant: HINOVA PHARMACEUTICALS INC., Chengdu (CN)

(72) Inventor: Yuanwei Chen, Chengdu (CN)

(73) Assignee: HINOVA PHARMACEUTICALS INC., Chengdu (CN)

( * ) Notice: Subject to any disclaimer, the term of this patent is extended or adjusted under 35 U.S.C. 154(b) by 0 days.

(21) Appl. No.: 14/364,147

(22) PCT Filed: Dec. 13, 2012

(86) PCT No.: PCT/CN2012/086573
§ 371 (c)(1),
(2) Date: Jun. 10, 2014

(87) PCT Pub. No.: WO2013/087004
PCT Pub. Date: Jun. 20, 2013

(65) Prior Publication Data
US 2014/0371284 A1  Dec. 18, 2014

(30) Foreign Application Priority Data

Dec. 14, 2011 (CN) .......................... 2011 1 0418859

(51) Int. Cl.
*C07D 235/02* (2006.01)
*C07D 233/86* (2006.01)
*A61K 31/4166* (2006.01)
*A61K 31/4184* (2006.01)
*C07D 233/72* (2006.01)

(52) U.S. Cl.
CPC .......... *C07D 235/02* (2013.01); *A61K 31/4166* (2013.01); *A61K 31/4184* (2013.01); *C07D 233/72* (2013.01); *C07D 233/86* (2013.01)

(58) Field of Classification Search
None
See application file for complete search history.

(56) References Cited

FOREIGN PATENT DOCUMENTS

| CN | 101817787 | A | 9/2010 |
|---|---|---|---|
| WO | 2006/124118 | A1 | 11/2006 |
| WO | 2007/126765 | A2 | 11/2007 |
| WO | 2007/126765 | A3 | 11/2007 |
| WO | 2007/127010 | A2 | 11/2007 |
| WO | 2007/127010 | A3 | 11/2007 |
| WO | WO2013/067151 | * | 5/2013 |

OTHER PUBLICATIONS

Ebede et al., Hormonal Treatment of Acne in Woman. The Journal of Clinical and Aesthetic Dermatology, 2009, 2, 16-22.*
Sinclair et al., Treatment of female pattern hair loss with oral antiandrogens. British Journal of Dermatology, 2005, 152, 466-473.*
Kushner et al., Pharmacological uses and perspectives of heavy water and deuterated compounds. Canadian Journal of Physiology and Pharmacology, 1999, 77, 79-88.*
Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Jung, Michael E. et al. "Structure-Activity Relationship for Thiohydantoin Androgen Receptor Antagonists for Castration-Resistant Prostate Cancer (CRPC)," *J. Med. Chem.* (2010) 53(7):2779-2796.
Martins, Andrew et al., "A Simple, Cost-Effective Method for the Regioselective Deuteration of Anilines," *Org. Lett.* (2008) 10(19): 4351-4353.
International Search Report (English Translation) corresponding to PCT/CN2012/086573 mailed Mar. 14, 2013, 6 pages.
Jiang, Wenfeng et al., "Application of Deuteration in Drug Research," *Qilu Pharmaceutical Affairs* (2010) 29(11):682-684, (Eng. abstract only).

* cited by examiner

*Primary Examiner* — Rebecca Anderson
*Assistant Examiner* — Po-Chih Chen
(74) *Attorney, Agent, or Firm* — Kilpatrick Townsend & Stockton LLP

(57) ABSTRACT

Provided are imidazolidinedione compounds of formula (I), processes for preparation, uses and pharmaceutically compositions thereof. The imidazolidinedione compounds posses androgen receptor antagonist activity and can be used for preventing and treating diseases and disorders related to androgen receptor, such as prostate cancer, alopecia, hair regeneration, acne and adolescent acne.

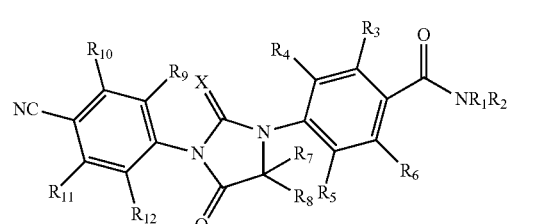

14 Claims, No Drawings

IMIDAZOLIDINEDIONE COMPOUNDS AND THEIR USES

TECHNICAL FIELD

The invention relates to the field of medicine, in particular, to imidazolidinedione compounds and uses thereof. More specifically, the invention relates to imidazolidinedione compounds and its use as androgen receptor antagonists or for the treatment and prevention of diseases related to androgen receptor.

BACKGROUND

Prostatic cancer (prostatic carcinoma, abbreviated as PCa) is the most common malignant neoplasmin in male reproductive system. The incidence thereof increases with age, and differs significantly from region to region, which is higher in U.S. and Europe. Second to lung cancer, prostatic cancer is the second cancer leading to death in men. In the past, prostatic cancer has not been paid attention in China, since it belongs to a small disease in the spectrum of tumor. However, with the social development and progress in our country, the aging of society, urbanization, westernization of dietary structure and advances in detection technology, the incidence of prostate cancer was significantly increased. A foreign survey about prostate cancer which was completed by The Second Hospital of Tianjin Medical University and Diagnosis and Treatment of Prostate cancer in Tianjin in 2011 showed that the incidence of prostate cancer in Tianjin was rapidly rising, the incidence of prostate cancer increased by 4 times in 20 years, and the number of patients with prostate cancer accounted for 13.4% of inpatient with urinary tract tumors. Prostatic cancer which was rare cancer in the past becomes common tumors. The incidence of prostate cancer has the same trend in China.

Androgen receptor is a ligand-dependent trans-transcriptional regulatory protein with 110,000 dalton molecular weight. Androgen receptor plays a very important role in the pathogen and deterioration process of prostate cancer, and in male hormone-related diseases such as acne, male alopecia, and so on.

Traditional methods for treating prostate cancer include surgery or using androgen receptor antagonists such as bicalutamide (Casodex). However, patients will develop drug resistance after 2-4 years treatment, while bicalutamide has side effects of stimulating the proliferation of cancer, therefore patients must stop using bicalutamide. Recent studies have found that bicalutamide will activate androgen receptors, thereby stimulating the proliferation of cancer.

Therefore, there is still a need in the art to develop compounds having superior pharmacodynamic properties to prostatic cancer.

SUMMARY OF INVENTION

The object of the invention is to provide a novel compound having androgen receptor antagonism and the use thereof.

In the first aspect of the invention, an imidazolidinedione compound of formula (I), or a crystal form, pharmaceutically acceptable salt, hydrate or solvate thereof is provided,

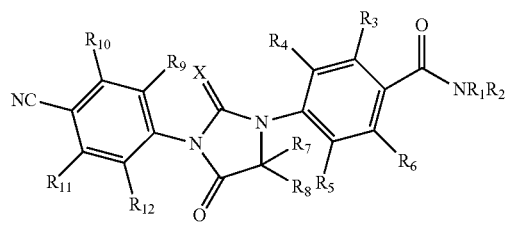

(I)

wherein, $R^1$ and $R^2$ are independently selected from hydrogen, deuterium, methyl and one or more deuterium-substituted or perdeuterated $C_1$-$C_4$ alkyl;

$R^3$ is hydrogen, deuterium or halogen;

$R^4$, $R^5$, $R^6$, $R^9$, $R^{10}$, $R^{12}$ are hydrogen, deuterium or halogen (such as F, Cl, Br, or I);

$R^7$ and $R^8$ are independently selected from methyl and one or more deuterium-substituted or perdeuterated $C_1$-$C_4$ alkyl, or $R^7$ and $R^8$ are joined to form $C_3$-$C_6$ (or $C_3$-$C_8$) cycloalkyl;

$R^{11}$ is non-deuterated, one or more deuterium-substituted or perdeuterated $C_1$-$C_4$ alkyl, or partly or totally halogen-substituted $C_1$-$C_4$ alkyl;

X is S or O;

provided that (1) at least one of $R^1$, $R^2$, $R^3$, $R^4$, $R^5$, $R^6$, $R^7$, $R^8$, $R^9$, $R^{10}$, $R^{11}$, $R^{12}$ is deuterated or is deuterium; or (2) When both of $R^1$ and $R^2$ is methyl, any group of $R^3$, $R^4$, $R^5$, $R^6$, $R^7$, $R^8$, $R^9$, $R^{10}$, $R^{11}$, $R^{12}$ can be deuterated or deuterium, or can be hydrogen or a non-deuterated.

In one embodiment, $R^1$ and $R^2$ are independently selected from hydrogen, deuterated methyl, and deuterated ethyl.

In one embodiment, when $R^1$ is hydrogen, $R^2$ is selected from the group consisting of mono-deuterated methyl, bi-deuterated methyl, tri-deuterated methyl, mono-deuterated ethyl, bi-deuterated ethyl, tri-deuterated ethyl, tetra-deuterated ethyl, and penta-deuterated ethyl.

In one embodiment, when $R^1$ is hydrogen, $R^2$ is tri-deuterated methyl.

In one embodiment, the compound is selected from the group consisting of

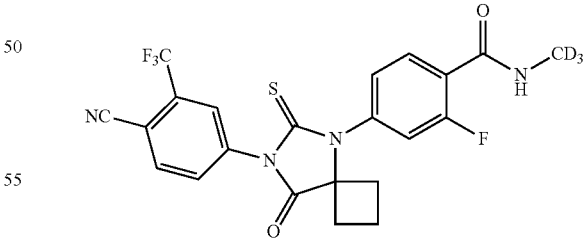

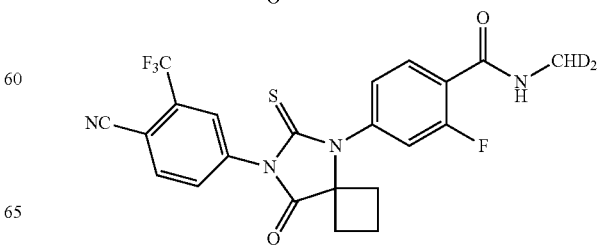

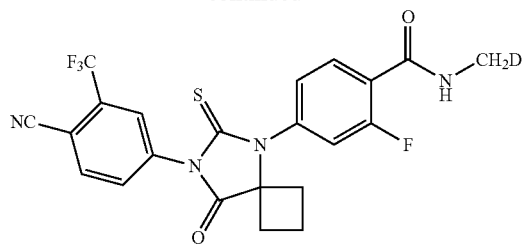
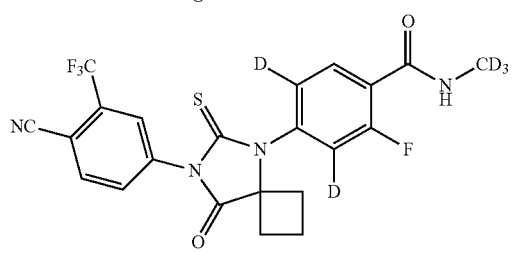
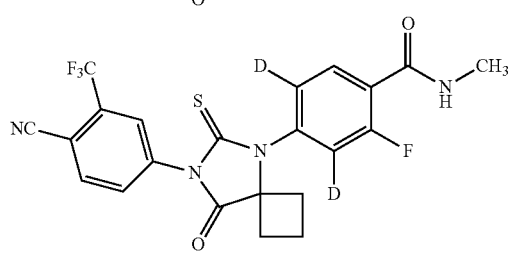
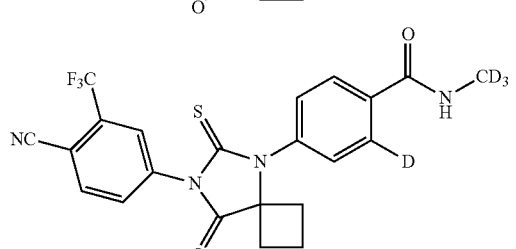
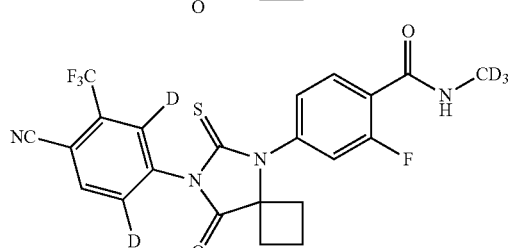
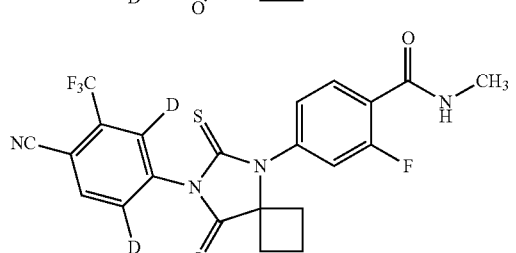
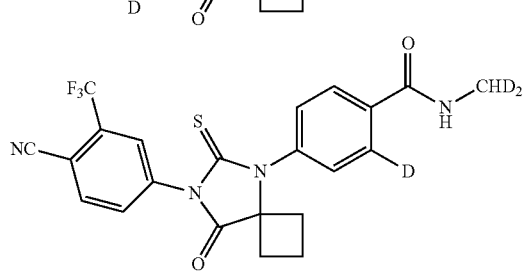
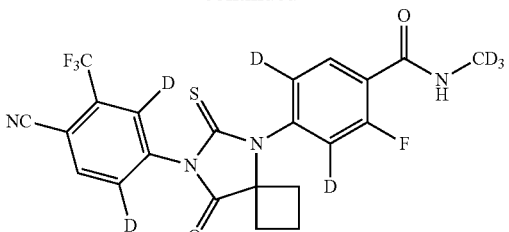
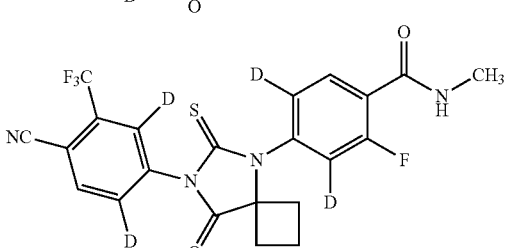
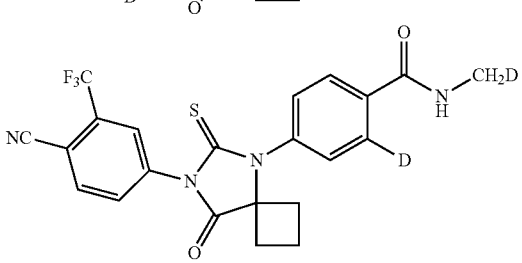
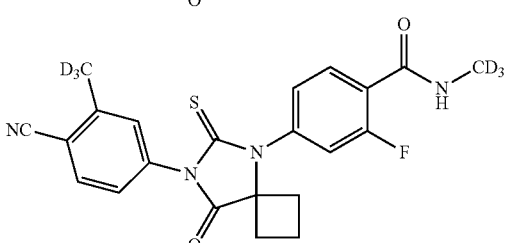
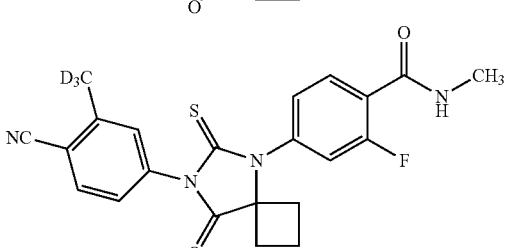
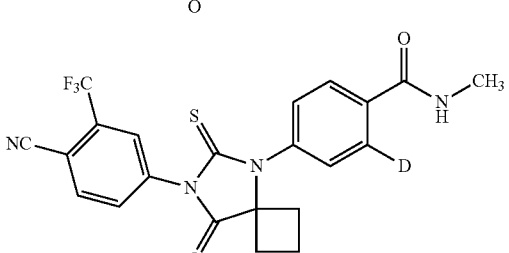
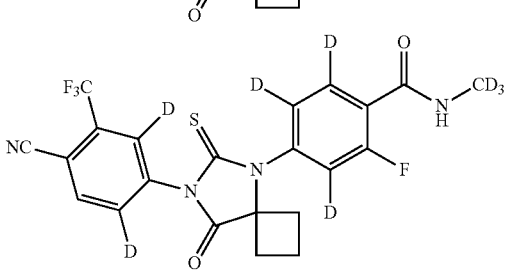

5
-continued
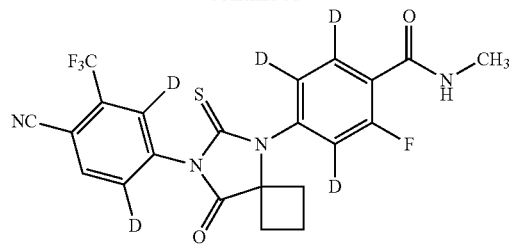
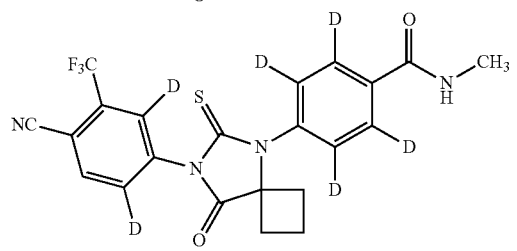
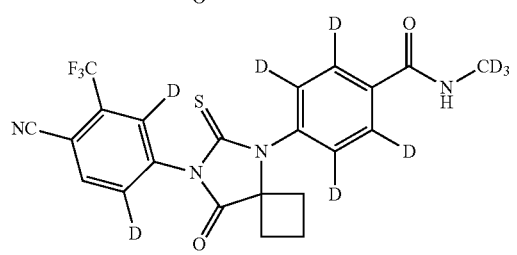
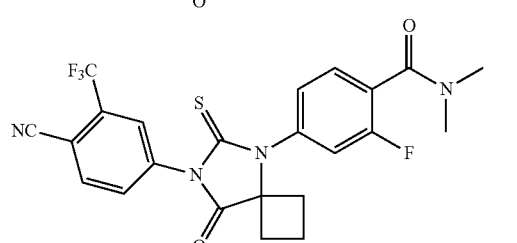
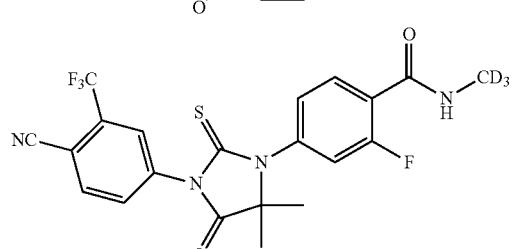
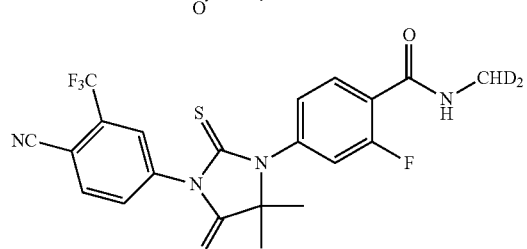
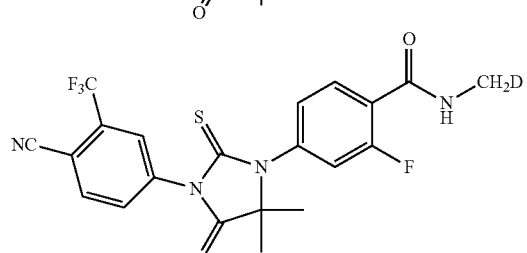
6
-continued
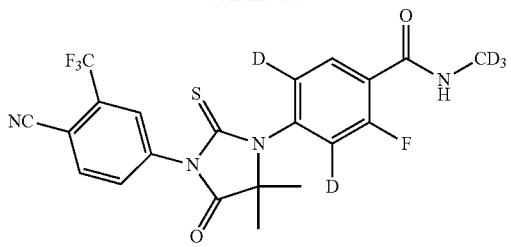
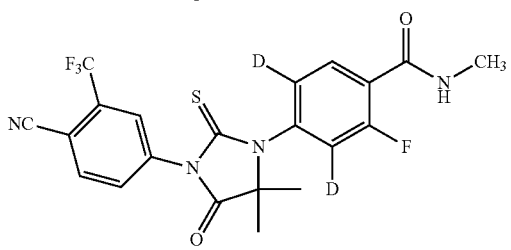
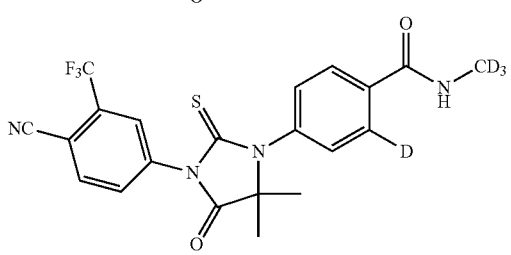
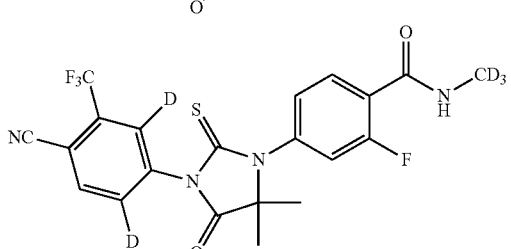
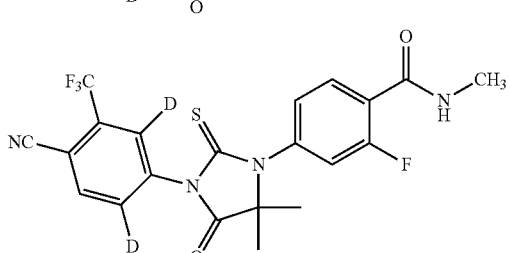
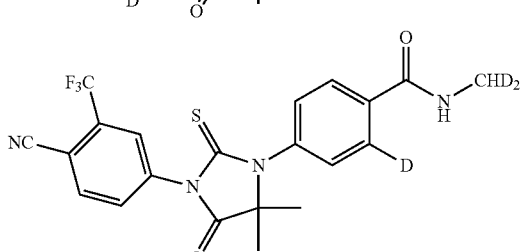
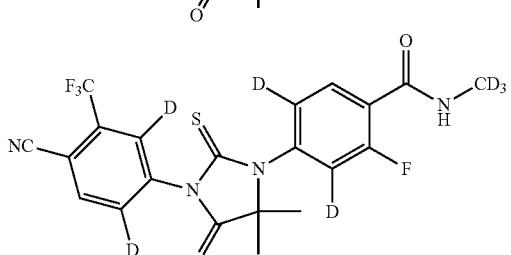

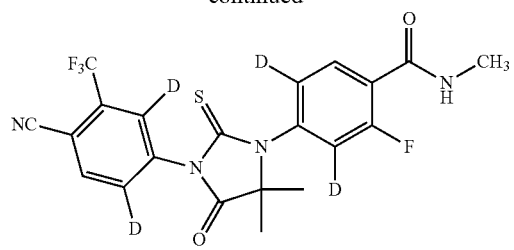
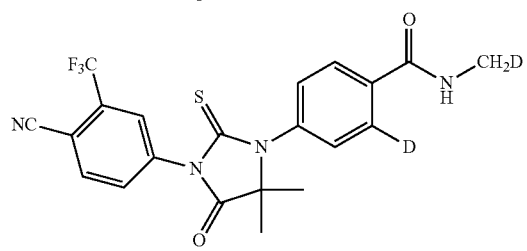
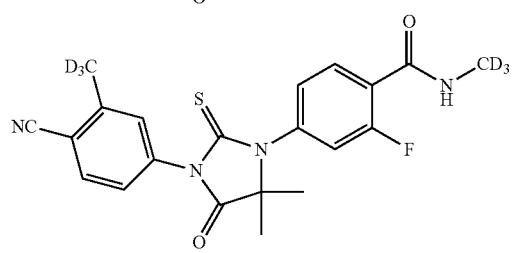
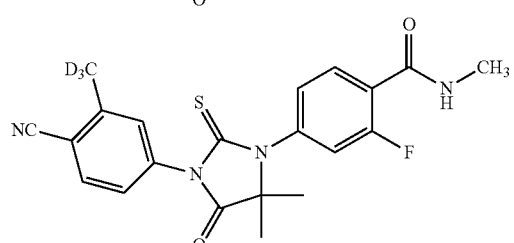
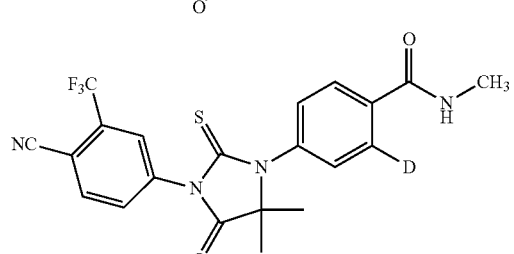
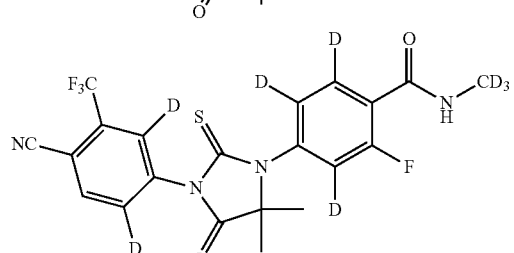
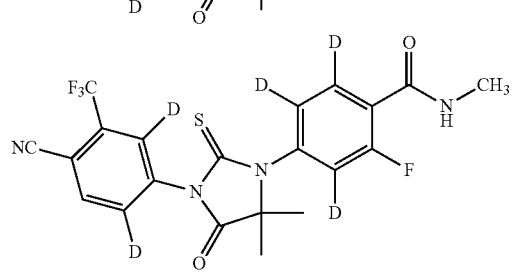
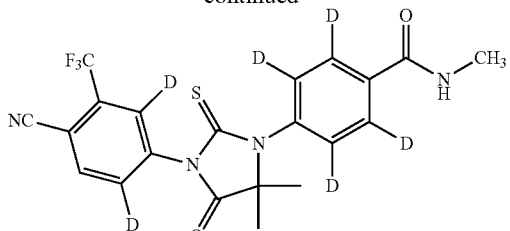
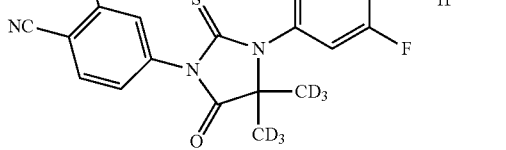
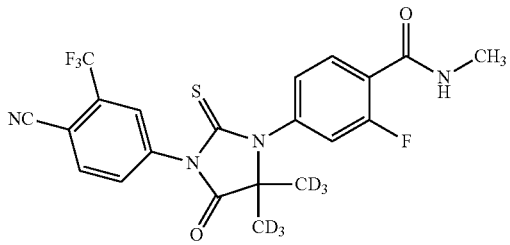
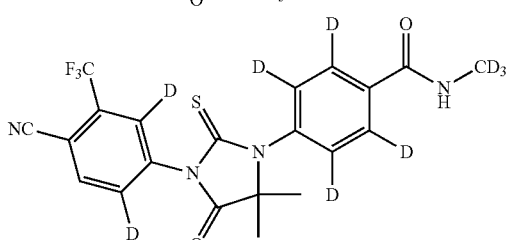
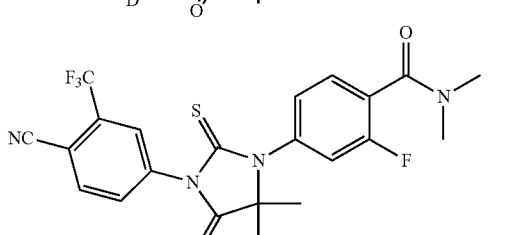
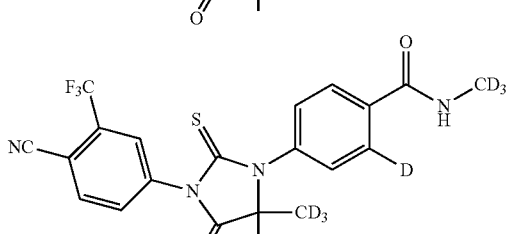
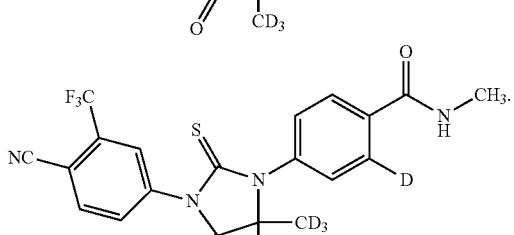

In one embodiment, the compound is selected from the group consisting of
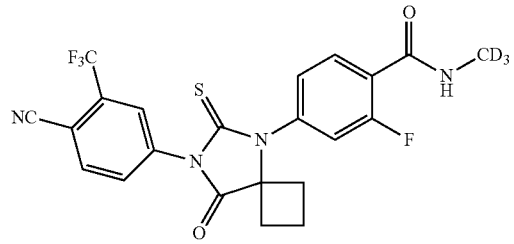
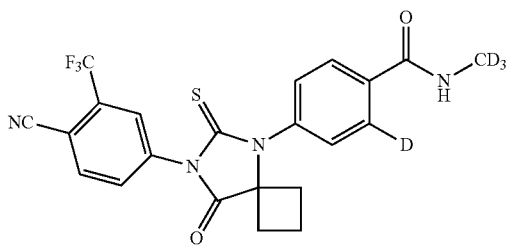
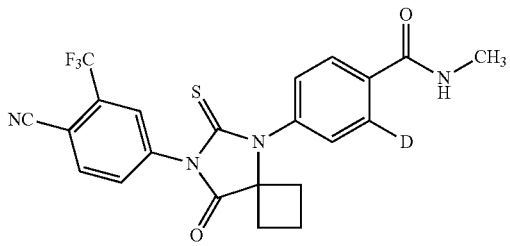
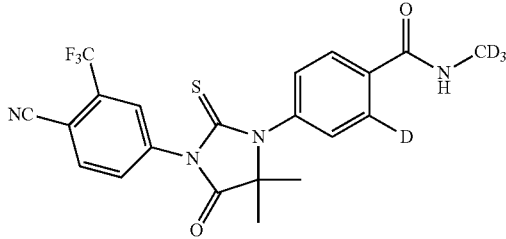
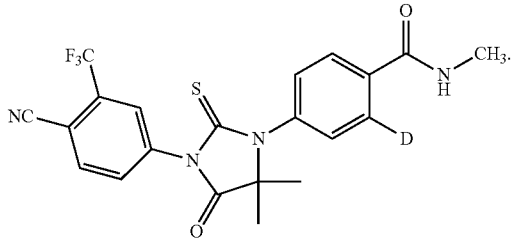
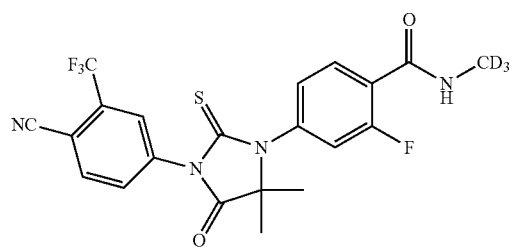
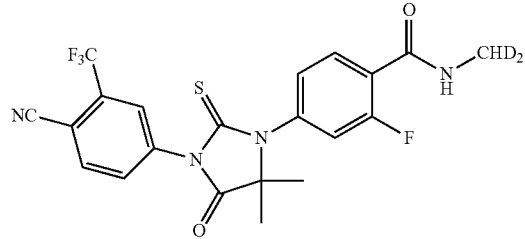
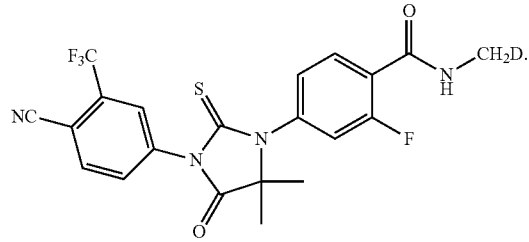
In one embodiment, the compound is selected from the group consisting of
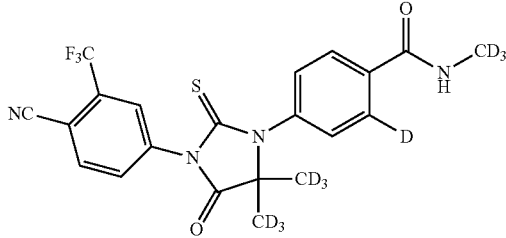
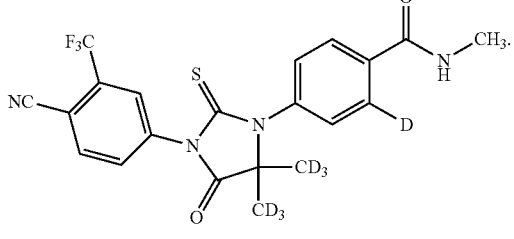
In one embodiment, the compound is selected from the group consisting of 4-[7-(4-cyano-2-trifluoromethyl-phenyl)-8-oxo-6-thio-5,7-diazaspiro[3,4]-5-octyl]-2-fluoro-N,N-dimethyl benzamide;

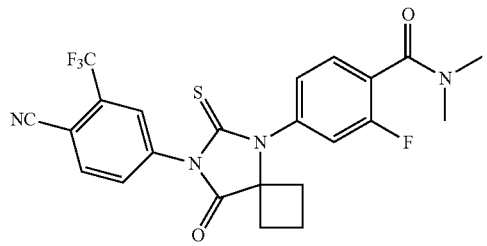 [SMILES: CN(C)C(=O)c1ccc(N2C(=S)N(c3ccc(C#N)c(C(F)(F)F)c3)C(=O)C23CCC3)cc1F]

4-{7-[4-cyano-3-(trifluoromethyl)phenyl]-5,5-dimethyl-4-oxo-2-thio-1-imidazolidinyl}-2-fluoro-N,N-dimethyl benzamide;

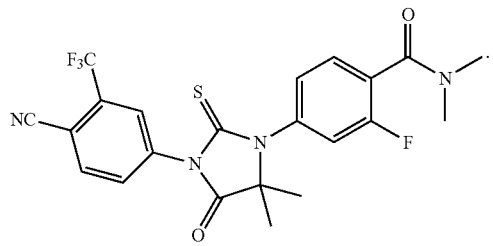 [SMILES: CN(C)C(=O)c1ccc(N2C(=S)N(c3ccc(C#N)c(C(F)(F)F)c3)C(=O)C2(C)C)cc1F]

In one embodiment, the compound is selected from the group consisting of
4-[7-(4-cyano-2-trifluoromethyl-phenyl)-8-oxo-6-thio-5,7-diazaspiro[3,4]-5-octyl]-2-fluoro-N-trideuteromethyl benzamide;

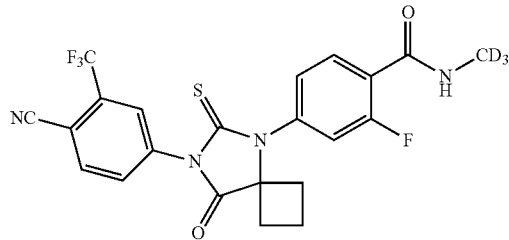 [SMILES: [2H]C([2H])([2H])NC(=O)c1ccc(N2C(=S)N(c3ccc(C#N)c(C(F)(F)F)c3)C(=O)C23CCC3)cc1F]

4-{7-[4-cyano-3-(trifluoromethyl)phenyl]-5,5-methyl-4-oxo-2-thio-1-imidazolidinyl}2-fluoro-N-trideuteromethyl benzamide;

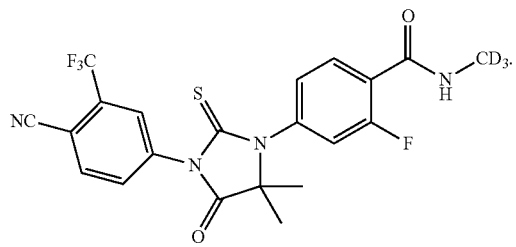 [SMILES: [2H]C([2H])([2H])NC(=O)c1ccc(N2C(=S)N(c3ccc(C#N)c(C(F)(F)F)c3)C(=O)C2(C)C)cc1F]

In the second aspect of the invention, a method for preparing a pharmaceutical composition is provided, comprising mixing the compound of the first aspect of the invention, or a crystal form, pharmaceutically acceptable salt, hydrate or solvate thereof and a pharmaceutically acceptable carrier to form a pharmaceutical composition.

In the third aspect of the invention, a pharmaceutical composition is provided, comprising (1) the compound of the first aspect of the invention, or a crystal form, pharmaceutically acceptable salt, hydrate or solvate thereof, and (2) a pharmaceutically acceptable carrier.

In one embodiment, the pharmaceutical composition further comprises an additional therapeutic agent; preferably, the additional therapeutic agent is the therapeutic agent for treating alopecia, hair regeneration, pimples, acne or prostate cancer.

In the forth aspect of the invention, provided is a use of the compound of the first aspect of the invention or a crystal form, pharmaceutically acceptable salt, hydrate or solvate thereof as an androgen receptor antagonist or for preparing drugs for treating and preventing diseases related to androgen receptor activity.

In one embodiment, the disease is selected from the group consisting of alopecia, hair regeneration, pimples, acne and prostate cancer.

In one embodiment, the composition is injection, capsules, tablets, pills, powder or granules.

In the fifth aspect of the invention, a treatment method is provided, comprising a step of administering the compound of the first aspect of the invention, or a crystal form, pharmaceutically acceptable salt, hydrate or solvate thereof or the pharmaceutical composition of the third aspect of the invention to a object in need thereof.

In one embodiment, the object is a person suffering from androgen receptor activity related disease.

In the sixth aspect of the invention, a method for preparing the compound of formula (I) of the first aspect of the invention is provided, comprising steps of:

(1) in a acidic solvent, in the presence of cyanide, reacting compound 5a with $R_7C(O)R_8$, to form compound 6a,

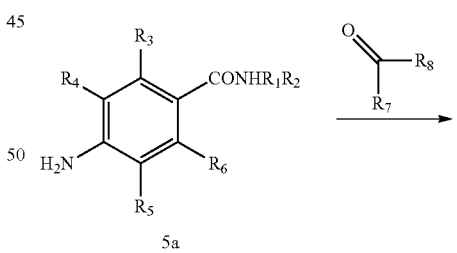

5a

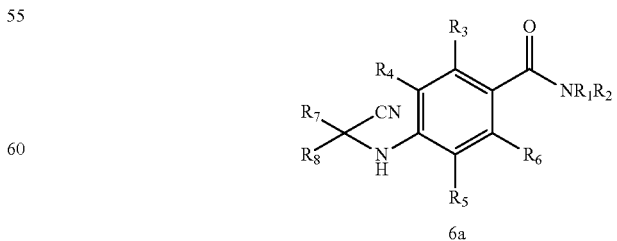

6a wherein, the cyanide is TMSCN, sodium cyanide or potassium cyanide, (2) in an aprotic solvent, under a acidic condition, reacting compound 2a with compound 6a, to form the compound of formula (I),

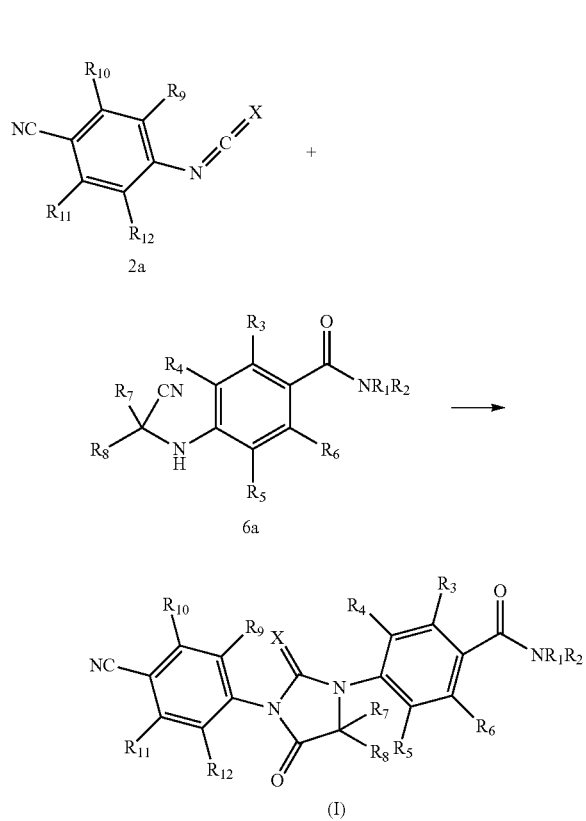

wherein, $R^1$, $R^2$, $R^3$, $R^4$, $R^5$, $R^6$, $R^7$, $R^8$, $R^9$, $R^{10}$, $R^{11}$, $R^{12}$ or X is defined as those in the first aspect of the invention.

In one embodiment, in step (2), the reaction is conducted in the presence of hydrochloric acid or sulfuric acid.

In one embodiment, the method further comprises the following steps prior to step (1):

(1-1) in an inert solvent, reacting compound 3a with $NHR_1R_2$, to form compound 4a, and

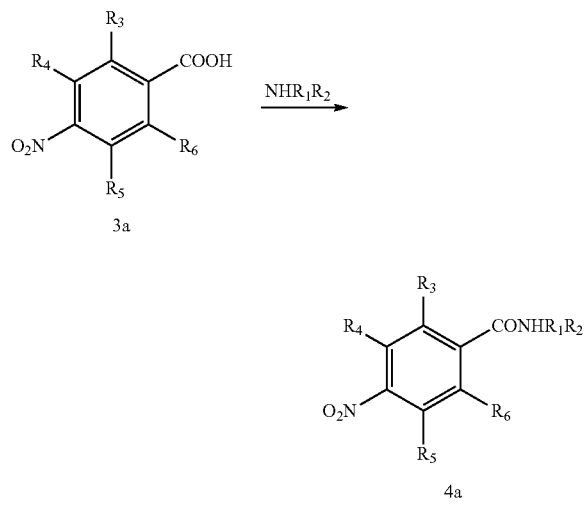

(1-2) in an inert solvent, reducing compound 4a to compound 5a,

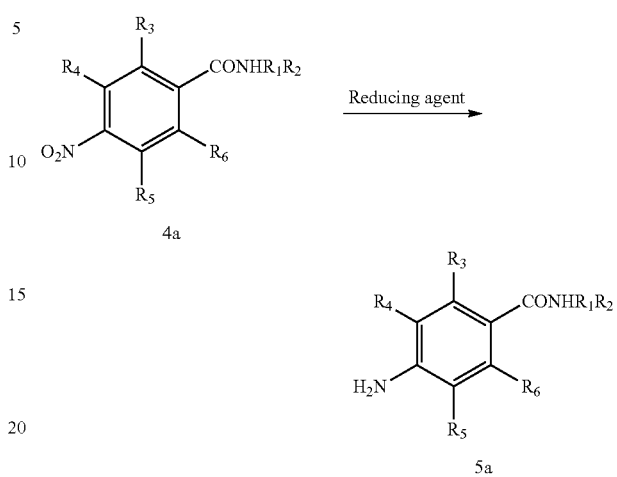

wherein, $R^1$, $R^2$, $R^3$, $R^4$, $R^5$, $R^6$ are defined as those in the first aspect of the invention.

In one embodiment, reduction is conducted with a reducing reagent selected from the group consisting of iron powder, zinc powder, and the combination thereof.

In one embodiment, the acidic solvent in step (1) is methanoic acid, acetic acid, an aqueous solution of hydrochloric acid with a mass concentration of 1-5% or an aqueous solution of sulfuric acid with a mass concentration of 1-5%.

In one embodiment, the aprotic solvent in step (2) is dimethyl formamide (DMF), dimethyl sulfoxide (DMSO), or $CH_3CN$.

In one embodiment, the inert solvent is methylene chloride, ethyl acetate, tetrahydrofuran, chloroform, or acetonitrile.

It should be understood that in the present invention, the technical features specifically described above and below (such as the Examples) can be combined with each other, thereby constituting a new or preferred technical solution, which needs not be specified.

DETAILED DESCRIPTION OF INVENTION

Through intensive research, the inventors unexpectedly discovers that, the imidazolidinedione compounds of formula (I) of the present invention, or a crystal form, pharmaceutically acceptable salt, hydrate or solvate thereof have excellent pharmacokinetics and/or pharmacodynamic properties, therefore are more suitably used as androgen receptor antagonists, and are more suitably used for the preparation of drugs for treating androgen-related diseases (such as cancer). Based on this discovery, the inventors complete the present invention.

Definition

As used herein, the term "halogen" refers to F, Cl, Br and I. Preferably, halogen is selected from F, Cl, and Br.

As used herein, the term "alkyl" refers to a straight chain or branched-chain alkyl. Preferably, alkyl is $C_1$-$C_4$ alkyl, such as methyl, ethyl, propyl, iso-propyl, butyl, iso-butyl, tert-butyl and the like.

As used herein, the term "deuterated" means that hydrogen(s) in a compound or group is substituted by deuterium(s). "Deuterated" can be mono-substituted, bi-substituted, multi-substituted or total-substituted. The terms "one or more deuterium-substituted" and "substituted by deuterium for once or more times" can be used interchangeably.

In one embodiment, the deuterium content in a deuterium-substituted position is greater than the natural abundance of deuterium (0.015%), preferably >50%, more preferably >75%, more preferably >95%, more preferably >97%, more preferably >99%, more preferably >99.5%.

Active Ingredients

As used herein, the term "compound of the invention" refers to the compound of formula (I). This term also includes various crystal forms, pharmaceutically acceptable salts, hydrates or solvates of the compound of formula (I).

As used herein, the term "pharmaceutically acceptable salt" refers to the salts which are suitable for medicine and formed by the compound of the invention with an acid or a base. Pharmaceutically acceptable salts include inorganic salts and organic salts. A preferred salt is formed by the compound of the invention with an acid. The acid suitable for forming salts includes, but not limited to, inorganic acid, such as hydrochloric acid, hydrobromic acid, hydrofluoric acid, sulfuric acid, nitric acid, phosphoric acid; organic acid, such as formic acid, acetic acid, propionic acid, oxalic acid, malonic acid, succinic acid, fumaric acid, maleic acid, lactic acid, malic acid, tartaric acid, citric acid, picric acid, methanesulfonic acid, benzene methanesulfonic acid, benzene sulfonic acid; and acidic amino acid, such as aspartic acid, glutamic acid.

Pharmaceutical composition and the administration thereof.

The compounds of the invention possess outstanding androgen receptor antagonism, therefore, the compounds of the invention and the crystal forms, the pharmaceutically acceptable inorganic or organic salts, hydrates or solvates thereof, and the pharmaceutical compositions comprising compounds of the invention as the main activity ingredient, can be used for treating, preventing and alleviating diseases mediated by androgen. According to the prior art, the compounds of the invention can be used to treat the following diseases: alopecia, hair regeneration, pimples, acne, or prostate cancer etc.

Pharmaceutical composition of the invention comprises a safe and effective amount of the compounds of the invention or the pharmaceutical acceptable salts thereof and pharmaceutically acceptable excipients or carriers. Wherein "safe and effective amount" refers to an amount of the compounds which is sufficient to improve the patient's condition and would not induce serious side effect. Generally, the pharmaceutical composition contains 1-2000 mg compounds of the invention/dose, preferably, 10-200 mg compounds of the invention/dose. Preferably, "one dose" refers to a capsule or tablet.

"Pharmaceutically acceptable carrier" means: one or more compatible solid or liquid fillers or gel material, which are suitable for human, and must have sufficient purity and sufficiently low toxicity. "Compatibility" herein means that the components of the compositions can be blended with the compounds of the invention or with each other, and would not significantly reduce the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

The application manner for the compounds or pharmaceutical compositions of the invention is not specially limited, and the representative application manner includes (but not limited to): oral, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and gum arabic; (c) humectant, such as, glycerol; (d) disintegrating agents such as agar, calcium carbonate, potato starch or tapioca starch, alginic acid, certain complex silicates, and sodium carbonate; (e) dissolution-retarding agents, such as paraffin; (f) absorption accelerators, for example, quaternary ammonium compounds; (g) wetting agents, such as cetyl alcohol and single glyceryl stearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffer.

The solid dosage forms such as tablets, sugar pills, capsules, pills and granules can be prepared by using coating and shell material, such as enteric coatings and other materials known in the art. They can contain opaque agent, and the release of the active compounds or compounds in such compositions can be delayed for releasing in certain portion of the digestive tract. Instance of the embedding components can be polymers and waxes. If necessary, the active compounds and one or more above excipients can be prepared into microcapsules.

Liquid dosage forms for oral administration include pharmaceutically acceptable emulsions, solutions, suspensions, syrups or tinctures. In addition to the active compounds, the liquid dosage forms may contain conventional inert diluent known in the art, such as water or other solvent, solubilizer and emulsifier, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the mixtures thereof and so on.

Besides the inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the mixtures thereof and so on.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and the suitable mixtures thereof.

The dosage forms of compounds of the invention for topical administration include ointments, powders, patches, aerosol, and inhalants. The active ingredients are mixed with physiologically acceptable carriers and any preservatives, buffers, or propellant if necessary, under sterile conditions.

The compounds of the invention can be administered alone, or in combination with other pharmaceutically acceptable compounds.

When the pharmaceutical compositions are used, a safe and effective amount of compounds of the present invention is applied to mammals in need thereof (such as human), wherein the applied amount is the pharmaceutically effective amount. For a person weighted 60 kg, the daily dose is usually 1~2000 mg, preferably 20~500 mg. Of course, the particular dose should also depend on other factors, such as the route of administration, patient healthy status etc, which are well within the skill of a skilled physician.

Preparation

The preparation methods of compound (I) of the present invention are described in detail as below. However, these specific methods are not provided for the limitation of the invention. The compounds of the invention can be readily prepared by optionally combining any of the various methods described in the specification or various methods known in the art, and such combination can readily be carried out by the skilled in the art.

The compound of formula (I) of the present invention can be prepared according to the following synthetic scheme. In general, during the preparation, each reaction is conducted in solvent, at a temperature between room temperature to reflux temperature (such as 0-120° C., preferably 0-80° C.). Generally, the reaction time is 0.1-60 hours, preferably, 0.5-48 hours.

Preferably, the preparation method for compound (I) is as follows:

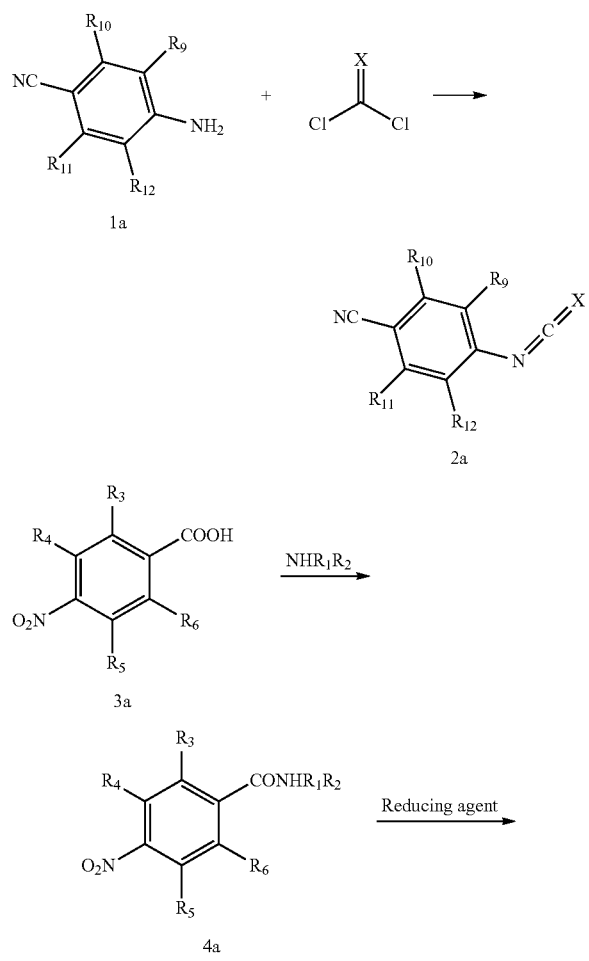

wherein $R^1$, $R^2$, $R^3$, $R^4$, $R^5$, $R^6$, $R^7$, $R^8$, $R^9$, $R^{10}$, $R^{11}$, $R^{12}$ and X are defined as those in formula (I).

Compound 1a (deuterated or non-deuterated aniline) reacts with thiophosgene (phosgene) to get compound 2a. Compound 4a can be synthesized by the amidation of compound 3a. The amine compound 5a can be obtained by reduction of compound 4a with reducing agent (such as zinc/acetic acid or iron/acetic acid). Compound 6a can be prepared by dehydration of aniline and ketones (e.g. $R_7C(O)R_8$) in the presence of TMSCN or cyanide (e.g. sodium cyanide or potassium cyanide). The final product (I) is synthesized by condensation of compound 2a and compound 6a under acidic conditions (such as hydrochloric acid or sulfuric acid).

The corresponding deuterated compounds can be prepared by using the corresponding starting deuterated compound or corresponding deuterated reagents as the starting material, such as deuterated methylamine, deuterated acetone and through the same route. The starting material with deuteration on benzene ring can be prepared by the following methods or literature (Org Letter. 2008, 4351-4353).

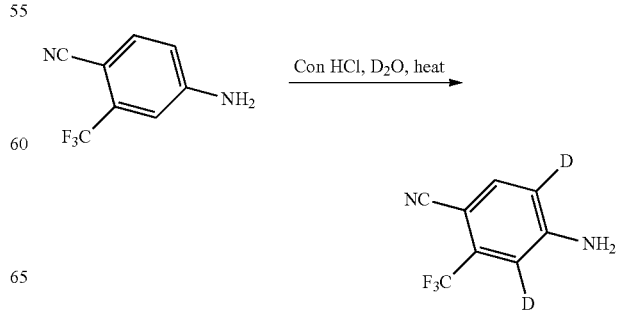

-continued

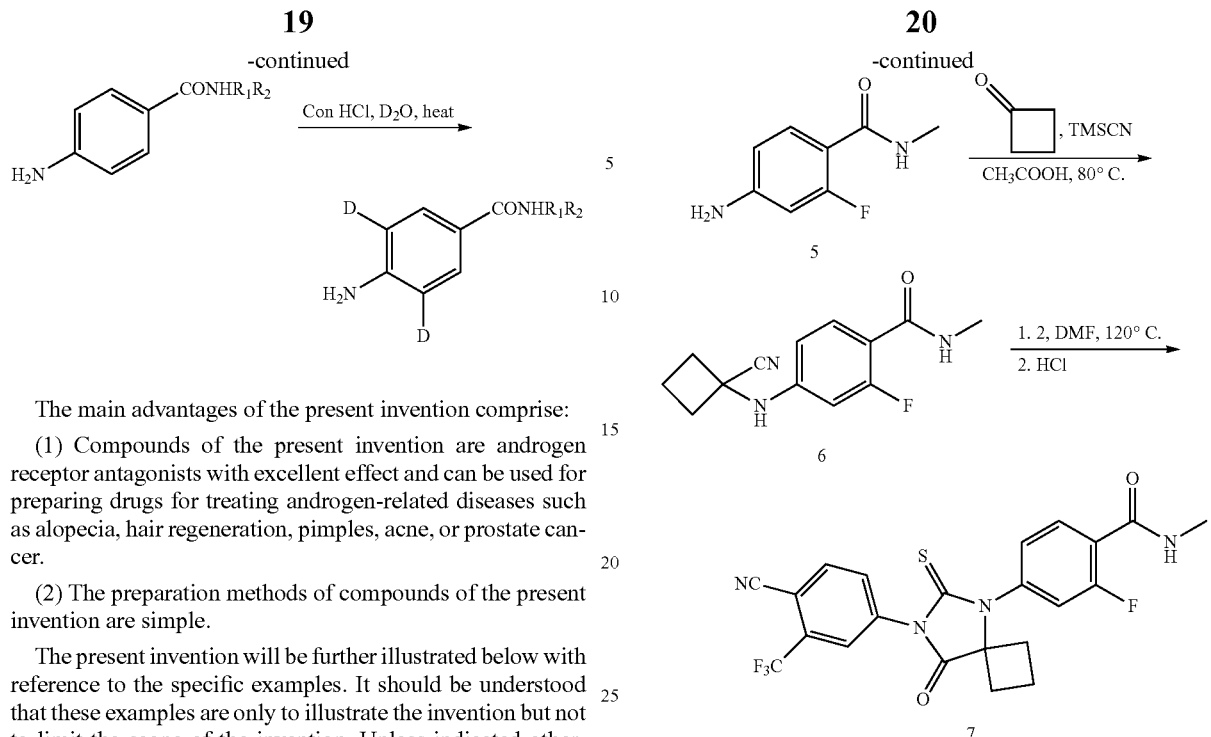

The main advantages of the present invention comprise:

(1) Compounds of the present invention are androgen receptor antagonists with excellent effect and can be used for preparing drugs for treating androgen-related diseases such as alopecia, hair regeneration, pimples, acne, or prostate cancer.

(2) The preparation methods of compounds of the present invention are simple.

The present invention will be further illustrated below with reference to the specific examples. It should be understood that these examples are only to illustrate the invention but not to limit the scope of the invention. Unless indicated otherwise, parts and percentage are calculated by weight.

The "reflux" refers to reflux, the "M.W." refers to microwave, "Con HCl" represents concentrated hydrochloric acid.

Example 1

4-[7-(4-cyano-2-trifluoromethyl-phenyl)-8-oxo-6-thio-5,7-diazaspiro[3,4]-5-octyl]-2-fluoro-N-methyl benzamide (compound 7, as control compound 1)

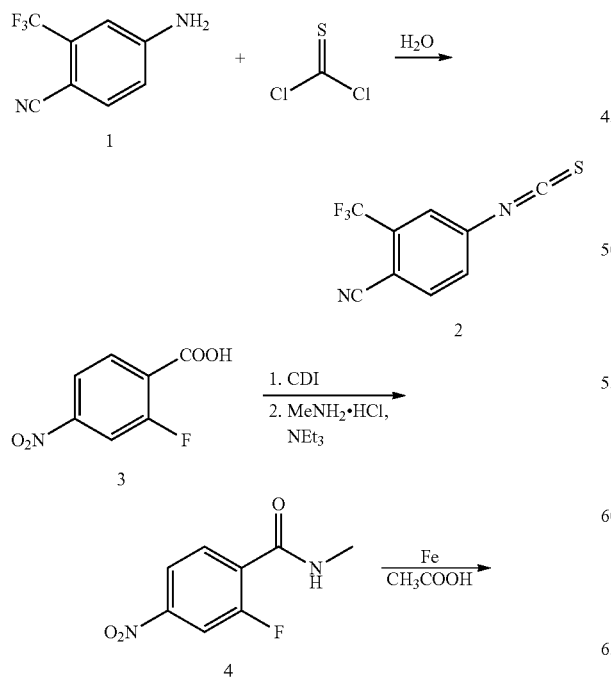

Synthesis of 4-isothiocyanato-2-(trifluoromethyl)-benzyl cyanide (compound 2)

Into an aqueous suspension (50 mL) of thiophosgene (30.2 g, 262.4 mmol) compound 1 (10.0 g, 53.7 mmol) was slowly added in portions. The reaction mixture was stirred at room temperature (20° C.) for one hour and then extracted with ethyl acetate for three times (3×50 mL). The organic layer was combined, washed with saturated brine (100 mL), dried ($Na_2SO_4$), filtered and concentrated under reduced pressure to give a black solid. After purified by column chromatography, a white solid (Compound 2, 11.24 g, yield 92%) was obtained. $^1$H NMR (CDCl$_3$, 400 MHz): δ(ppm) 7.85 (1H, d, J=8 Hz), 7.59 (1H, s), 7.48 (1H, d, J=8.4 Hz). MS: 229 (M+H$^+$).

Synthesis of 2-fluoro-N-methyl-4-nitro-benzamide (Compound 4)

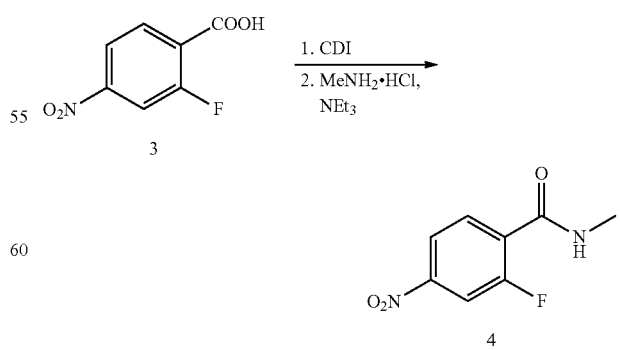

Into a dichloromethane solution (200 mL) of compound 3 (25.0 g, 135.06 mmol) CDI (32.8 g, 202.28 mmol) was added.

The reaction mixture was stirred at room temperature for one hour. Into a dichloromethane solution (50 mL) of methylamine hydrochloride (10.94 g, 162.12 mmol) triethylamine (20.47 g, 202.29 mmol) was added to give a white suspension which was then stirred at room temperature for half an hour. Afterwards, the suspension was slowly added to the reaction mixture. The resulting mixture was stirred for another hour, and then the reaction was quenched by water (100 mL). The organic phase was separated, the aqueous phase was extracted twice with dichloromethane (2×50 mL), and then the organic phases were combined, washed with 1 M hydrochloric acid twice (2×50 mL), 1 M aqueous sodium hydroxide solution twice (2×50 mL) and saturated brine (100 mL) once, dried (Na$_2$SO$_4$), filtered and concentrated under reduced pressure to give a white solid 4 (compound 4, 14.6 g, yield 55%). MS: 199 (M+H$^+$).

Synthesis of 2-fluoro-N-methyl-4-amino-benzamide (Compound 5)

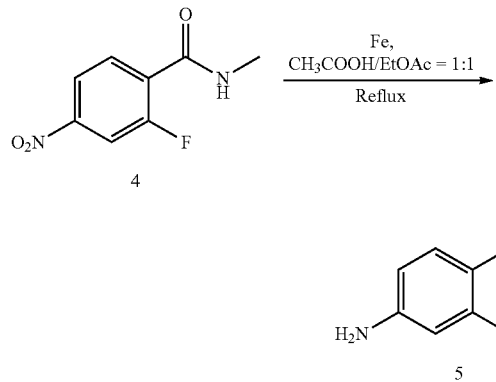

Compound 4 (14.6 g, 73.7 mmol) was dissolved in a solution of ethyl acetate and acetic acid (50 mL+50 mL). Then 39 g of iron powder was added. The resulting mixture was refluxed overnight (16 h), then cooled to room temperature. The solid was filtered and washed with ethyl acetate for three times (3×50 mL). The organic phases were combined, washed with brine, dried over sodium sulfate and concentrated to give a yellow solid which was purified by column chromatography (DCM:MeOH=50:1), to give a pale yellow solid, compound 5 (7.62 g, yield 61.5%). $^1$H NMR (CDCl$_3$, 400 MHz): δ(ppm) 7.92 (1H, t, J=8.8 Hz), 6.60 (1H, s), 6.49 (1H, d, J=8.4 Hz), 6.32 (1H, d, J=14 Hz), 4.10 (2H, s), 2.99 (3H, d, J=4.4 Hz).

Synthesis of 4-(1-cyano-cyclobutylamino)-2-fluoro-N-methyl-benzamide (Compound 6)

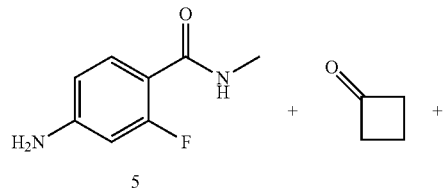

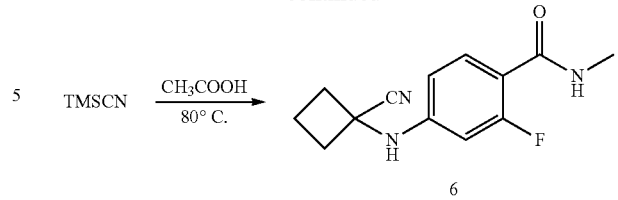

TMSCN (1.77 g, 17.84 mmol), cyclobutanone (0.89 mL, 11.89 mmol) and compound 5 (1 g, 5.95 mmol) were dissolved in acetic acid (10 mL). The resulting mixture was reacted at 80° C. overnight (16 h). After cooled to room temperature, into the mixture water (10 mL) was added and extracted with ethyl acetate, washed with brine, dried over sodium sulfate and concentrated. The resulting solid was washed with petroleum ether (10 mL) and dried by suction to give compound 6 as a brown solid (1.32 g, yield 90%). $^1$H NMR (CDCl$_3$, 400 MHz): δ(ppm) 7.99 (1H, t, J=8.4 Hz), 6.70 (1H, s), 6.49 (1H, d, J=8.8 Hz), 6.30 (1H, d, J=14.4 Hz), 4.62 (1H, s), 3.01 (3H, d, J=4.8 Hz), 2.84 (2H, m), 2.40 (2H, m), 2.27 (1H, m), 2.20 (1H, m).

5. Synthesis of 4-[7-(4-cyano-2-trifluoromethyl-phenyl)-8-oxo-6-thio-5,7-diazaspiro (compound 7, control compound 1)

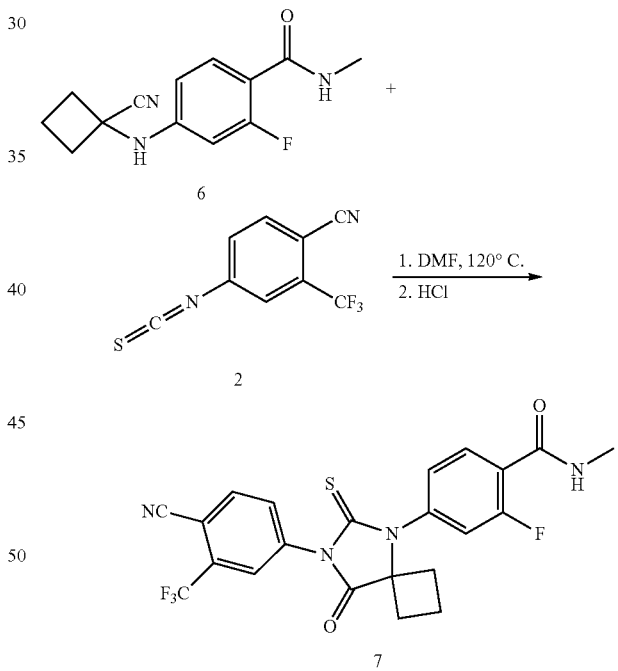

Compound 6 (1 g, 4.04 mmol) and Compound 2 (0.92 g, 4.04 mmol) were dissolved in DMF (10 mL). The obtained mixture was heated to 120° C. overnight (16 h), and then ethanol (10 mL), water (10 mL) and concentrated hydrochloric acid (2 mL) were added and heated at reflux for 1 h. The resulting mixture was extracted with ethyl acetate, washed with brine, dried over sodium sulfate, concentrated and purified by column chromatography (PE:EA/1:1) to give a brown solid, which was purified by preparative chromatography to give compound 7 as a white solid (210 mg, yield 11%). $^1$H NMR (DMSO, 400 MHz): δ(ppm) 8.48 (1H, s), 8.40 (1H, d, J=8 Hz), 8.25 (1H, s), 8.06 (1H, d, J=8.4 Hz), 7.83 (1H, t, J=7.6 Hz), 7.48 (1H, d, J=10.4 Hz), 7.39 (1H, d, J=8.4 Hz), 2.81 (3H, d), 2.63 (2H, m), 2.48 (2H, m), 1.96 (1H, m), 1.58 (1H, m). MS: 477.2 (M+H$^+$).

Example 2

4-[7-(4-cyano-2-trifluoromethyl-phenyl)-8-oxo-6-thio-5,7-diazaspiro[3,4]-5-octyl]-2-fluoro-N,N-dimethyl benzamide (Compound 11)

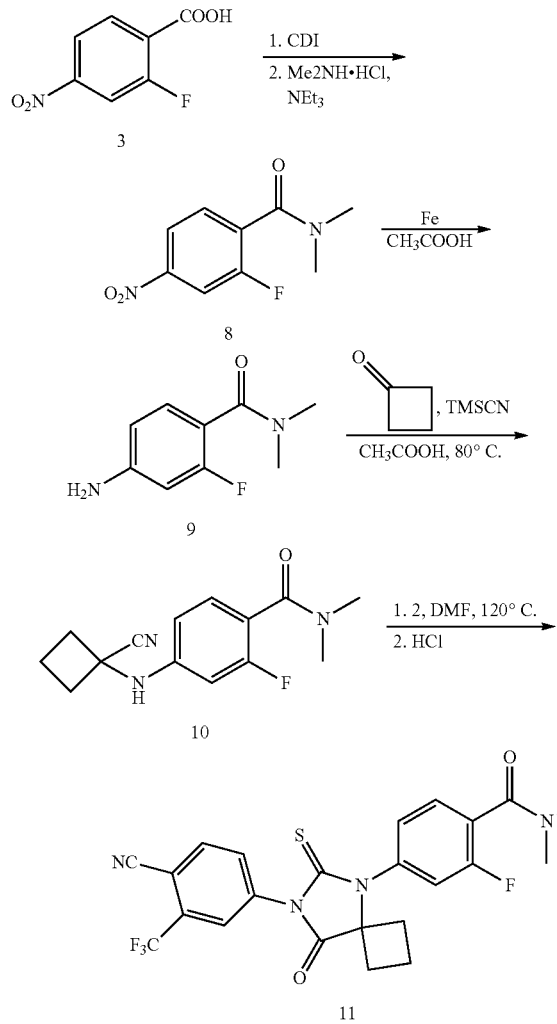

Synthesis of 2-fluoro-N,N-dimethyl-4-nitro-benzamide (Compound 8)

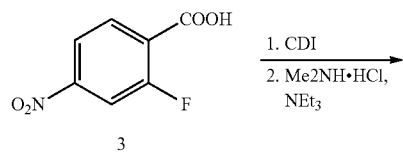

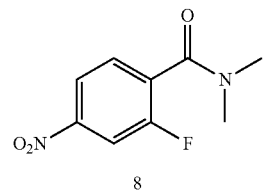

Into a solution of compound 3 (25 g, 135.06 mol) in methylene chloride (200 mL)

CDI (32.8 g, 202.28 mmol) was added. The reaction mixture was stirred at room temperature for one hour. Into a solution of dimethylamine hydrochloride (13.22 g, 162.12 mmol) in dichloromethane (50 mL) triethylamine (20.47 g, 202.29 mmol) was added to give a white suspension. After stirred at room temperature for half an hour, the suspension was added to the reaction mixture slowly. After the resulting mixture was stirred for one hour, the reaction was quenched by adding water (100 mL). The organic phase was separated and the aqueous phase was extracted with dichloromethane twice (2×50 mL). The organic phases were combined, washed with 1 M hydrochloric acid twice (2×50 mL), 1 M aqueous sodium hydroxide solution twice (2×50 mL) and saturated brine (100 mL) once, dried (Na$_2$SO$_4$), filtered and concentrated under reduced pressure to give a white solid 8 (compound 8, 16.86 g, yield 60%). MS: 199 (M+H$^+$).

Synthesis of 2-fluoro-N,N-dimethyl-4-amino-benzamide (Compound 9)

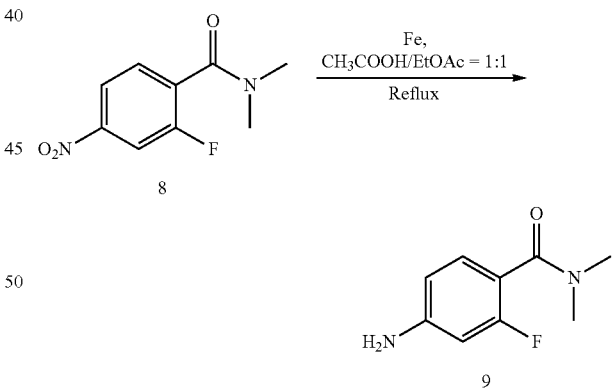

Compound 8 (16.86 g, 79.5 mmol) was dissolved in a solution of ethyl acetate and acetic acid (60 mL+60 mL). 42 g of iron powder was added and the mixture was refluxed overnight (16 h), and then cooled to room temperature. The solid was filtered, and washed with ethyl acetate (3×60 mL) for three times. The organic phases were combined, washed with brine, dried over sodium sulfate, and concentrated to give a yellow solid which was purified by column chromatography (DCM:MeOH=50:1) to give compound 9 as a white solid (7.8 g, 55% yield).

Synthesis of 4-(1-cyano-cyclobutylamino)-2-fluoro-N,N-dimethyl-benzamide (compound 10)

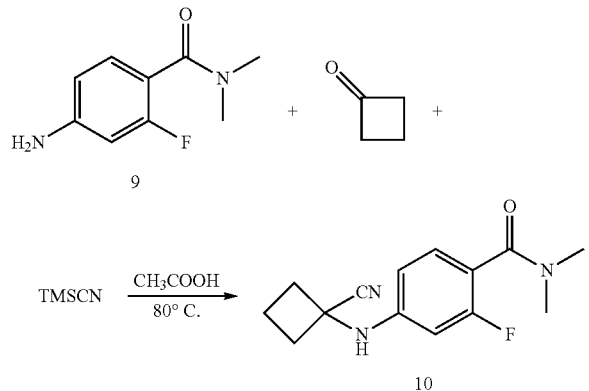

TMSCN (1.63 g, 16.47 mmol), cyclobutanone (0.82 mL, 10.98 mmol), compound 9 (1 g, 5.49 mmol) were dissolved in acetic acid (10 mL). The resulting mixture was maintained at 80° C. overnight (16 h), and cooled to room temperature. Water (10 mL) was added, and the resulting mixture was extracted with ethyl acetate, washed with brine, dried over sodium sulfate, and concentrated. The resulting solid was washed with petroleum ether (10 mL) and dried by suction to give compound 11 as a brown solid (1.31 g, yield 91%). $^1$H NMR (DMSO, 400 MHz): δ(ppm) 7.24 (1H, s), 7.20 (1H, d, J=8 Hz), 6.46 (1H, d, J=8.8 Hz), 6.33 (1 H, d, J=12 Hz) 2.96 (3H, s), 2.87 (3H, s), 2.74 (2H, m), 2.36 (2H, m), 2.08 (2H, m).

Synthesis of 4-[7-(4-cyano-2-trifluoromethyl-phenyl)-8-oxo-6-thio-5,7-diazaspiro[3,4]-5-octyl]-2-fluoro-N,N-dimethyl-benzamide (compound 11)

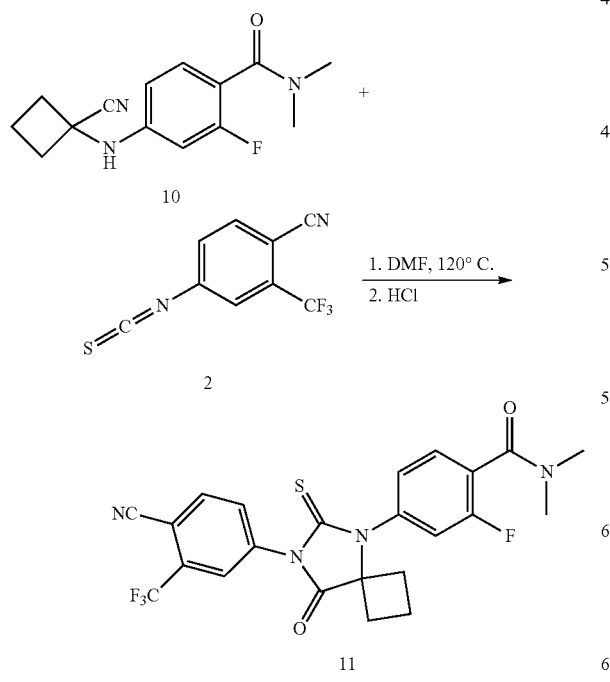

Compound 10 (1 g, 3.83 mmol) and compound 2 (1 g, 4.38 mmol) were dissolved in DMF (10 mL). The mixture was heated to 120° C. and kept overnight (16 h). Ethanol (10 mL), water (10 mL) and concentrated hydrochloric acid (2 mL) were added, and the resulting mixture was heated at reflux for 1 h. The mixture was extracted with ethyl acetate, washed with brine, dried over sodium sulfate, and concentrated. A brown solid was obtained by column chromatography (PE: EA/1:1), which was further purified by preparative chromatography to give compound 11 as a white solid (256.5 mg, yield 13.6%). $^1$H NMR (DMSO, 400 MHz): δ(ppm) 8.40 (1H, d, J=8.4 Hz), 8.25 (1H, s), 8.06 (1H, d, J=8.4 Hz), 7.65 (1H, t, J=7.6 Hz), 7.49 (1H, d, J=9.6 Hz), 7.39 (1 H, d, J=8 Hz), 3.05 (3H, s), 2.91 (3H, s), 2.64 (2H, m), 2.50 (2H, m), 1.97 (1H, m), 1.59 (1H, m). MS: 491.2 (M+H$^+$).

Example 3

4-[7-(4-cyano-2-trifluoromethyl-phenyl)-8-oxo-6-thio-5,7-diazaspiro[3,4]-5-octyl]-2-fluoro-N-trideuteromethyl-benzamide (compound 15)

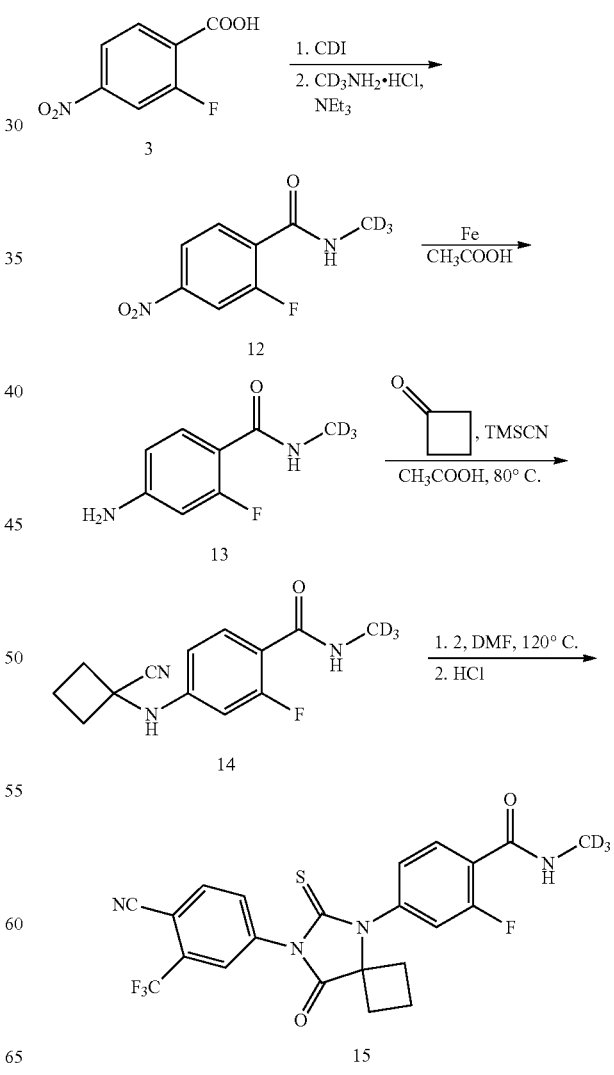

Synthesis of 2-fluoro-N-trideuteromethyl-4-nitro-benzamide (compound 12)

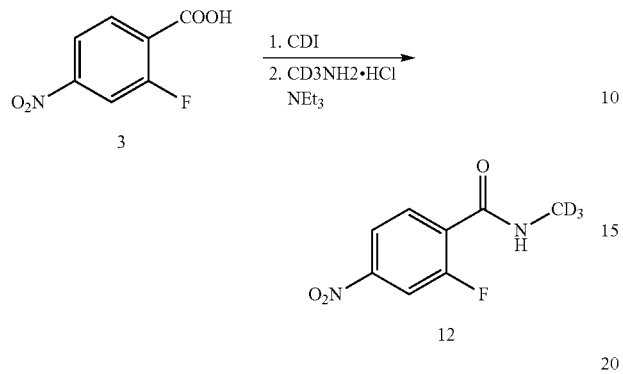

Into a solution of compound 3 (5.25 g, 28.37 mol) in dichloromethane (20 mL) CDI (4.62 g, 28.37 mmol) was added. The reaction mixture was stirred at room temperature for one hour. Into a solution of trideuterated methylamine hydrochloride (2 g, 28.76 mmol) in methylene chloride (20 mL) triethylamine (3.27 g, 32.36 mmol) was added to give a white suspension. After stirred at room temperature for half an hour, the suspension was added to the reaction mixture slowly. The resulting mixture was stirred for another hour, the reaction was quenched by adding water (10 mL). The organic phase was separated and the aqueous phase was extracted with dichloromethane (2×20 mL) twice. The organic phases were combined, washed with 1 M hydrochloric acid (2×10 mL) twice, 1 M aqueous sodium hydroxide solution (2×10 mL) twice and saturated brine (10 mL) once, dried ($Na_2SO_4$), filtered and concentrated under reduced pressure to give a white solid 12 (compound 12, 5.1 g, 88.2% yield). MS: 202 ($M+H^+$).

Synthesis of 2-fluoro-N-trideuteromethyl-4-amino-benzamide (compound 13)

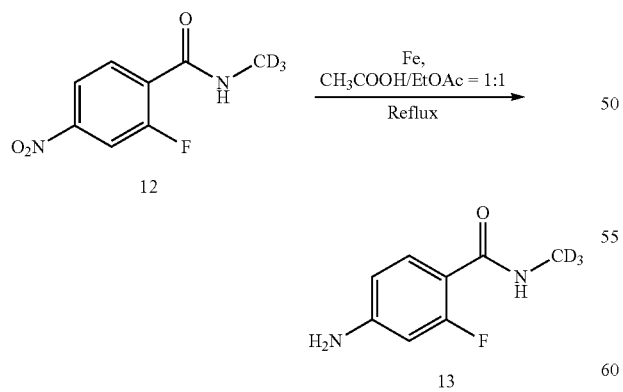

Compound 12 (5.1 g, 25.37 mmol) was dissolved in a solution of ethyl acetate and acetic acid (15 mL+15 mL). 15 g of iron powder was added and the mixture was refluxed overnight (16 h) and then cooled to room temperature. The solid was filtered, and washed with ethyl acetate (3×20 mL) for three times, the organic phases were combined, washed with brine, dried over sodium sulfate, and concentrated to give a yellow solid which was purified by column chromatography (DCM:MeOH=50:1) to give compound 13 as a pale yellow solid (2.22 g, 51.2% yield). $^1HNMR$ ($CDCl_3$, 400 MHz): δ(ppm) 7.92 (1H, t, J=8.8 Hz), 6.59 (1H, s), 6.49 (1H, d, J=8.4 Hz), 6.32 (1H, d, J=14.4 Hz), 4.10 (2H, s).

Synthesis of 4-(1-cyano-cyclobutylamino)-2-fluoro-N-trideuteromethyl-benzamide (compound 14)

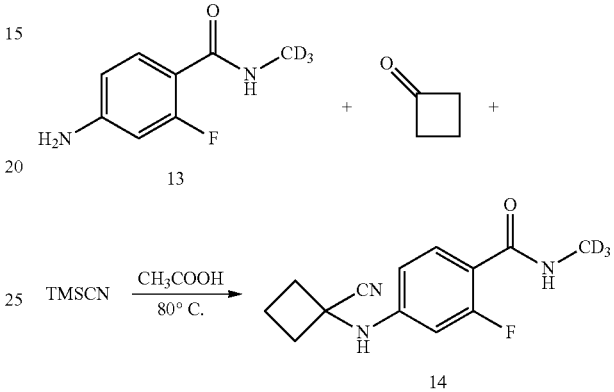

TMSCN (1.77 g, 17.54 mmol), cyclobutanone (0.89 mL, 11.88 mmol), and compound 13 (1 g, 5.95 mmol) were dissolved in acetic acid (10 mL). The mixture was maintained at 80° C. overnight (16 h), and cooled to room temperature. Water (10 mL) was added, and the resulting mixture was extracted with ethyl acetate, washed with brine, dried over sodium sulfate, and concentrated. The resulting solid was washed with petroleum ether (10 mL) and dried by suction to give compound 14 as a brown solid (1.31 g, 90% yield). $^1H$ NMR (DMSO, 400 MHz): δ(ppm) 7.79 (1H, s), 7.56 (1H, t, J=8.8 Hz), 7.36 (1H, s), 6.46 (1H, d, J=8.4 Hz), 6.31 (1H, d, J=13.6 Hz), 2.76 (2H, m), 2.36 (2H, m), 2.07 (2H, m). MS: 251.1 ($M+H^+$).

Synthesis of 4-[7-(4-cyano-2-trifluoromethyl-phenyl)-8-oxo-6-thio-5,7-diazaspiro[3,4]-5-octyl]-2-fluoro-N-trideuteromethyl-benzamide (compound 15)

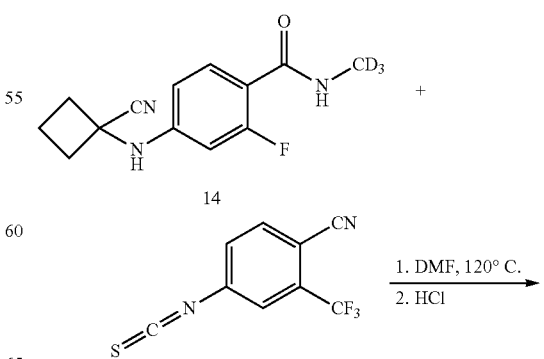

-continued

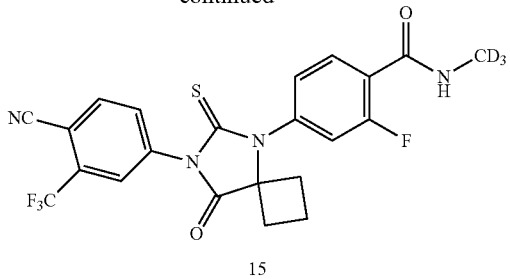

15

Compound 14 (0.5 g, 2 mmol) and Compound 2 (0.5 g, 2.19 mmol) were dissolved in DMF (5 mL). The resulting solution was heated to 120° C. overnight (16 h). Into the solution ethanol (5 mL), water (5 mL) and concentrated hydrochloric acid (1 mL) were added, and the resulting mixture was heated at reflux for 1 h. The resulting mixture was extracted with ethyl acetate, washed with brine, dried over sodium sulfate, and concentrated. The residue was purified by column chromatography (PE:EA/1:1) to give a brown solid which was further purified by preparative chromatography to give compound 15 as a white solid (204.6 mg, 21.36% yield). $^1$H NMR (DMSO, 400 MHz): δ(ppm) 8.46 (1H, s), 8.40 (1H, d, J=8 Hz), 8.25 (1H, s), 8.06 (1H, d, J=8 Hz), 7.83 (1H, t, J=8 Hz), 7.48 (1H, d, J=10.8 Hz), 7.39 (1H, d, J=8.4 Hz), 2.64 (2H, m), 2.47 (2H, m), 1.97 (1H, m), 1.57 (1H, m) o 477.2 (M+H$^+$).

Example 4

4-{7-[4-cyano-3-(trifluoromethyl)phenyl]-5,5-dimethyl-4-oxo-2-thio-1-imidazolidinyl}-2-fluoro-N-methyl-benzamide (compound 17, as a control compound 2)

Synthesis of 4-(2-cyano-2-propylamino)-2-fluoro-N-methyl-benzamide (compound 16)

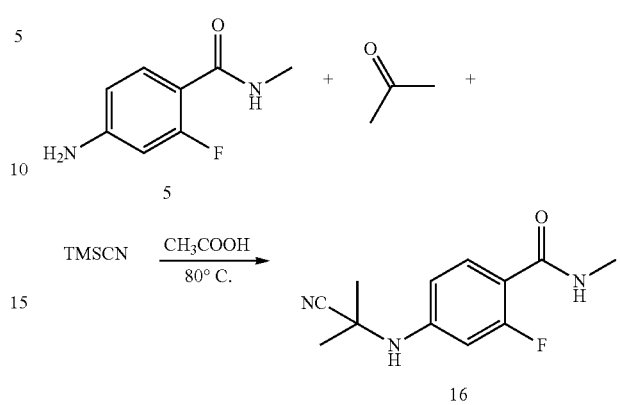

TMSCN (5 g, 50.4 mmol) and compound 5 (2 g, 11.89 mmol) were dissolved in a mixed solution of acetic acid (10 mL) and acetone (10 mL). The resulting mixture was maintained in a sealed tube at 80° C. overnight (16 h), and then cooled to room temperature. Acetone was removed under reduced pressure, water was added (20 mL), and the resulting mixture was extracted with ethyl acetate, washed with brine, dried over sodium sulfate, and concentrated. The resulting solid was washed with petroleum ether (10 mL) and dried by suction to give compound 16 as a white solid (2.56 g, 91.5% yield). $^1$H NMR (CDCl$_3$, 400 MHz): δ(ppm) 7.97 (1H, t, J=8.8 Hz), 6.65 (1H, s), 6.62 (1H, d, J=5.2 Hz), 6.59 (1H, d, J=14.8 Hz), 4.40 (1H, s), 3.01 (3H, d, J=4 Hz), 1.76 (6H, s).

Synthesis of 4-{7-[4-cyano-3-(trifluoromethyl)phenyl]-5,5-dimethyl-4-oxo-2-thio-1-imidazolidinyl}-2-fluoro-N-methyl-benzamide (compound 17)

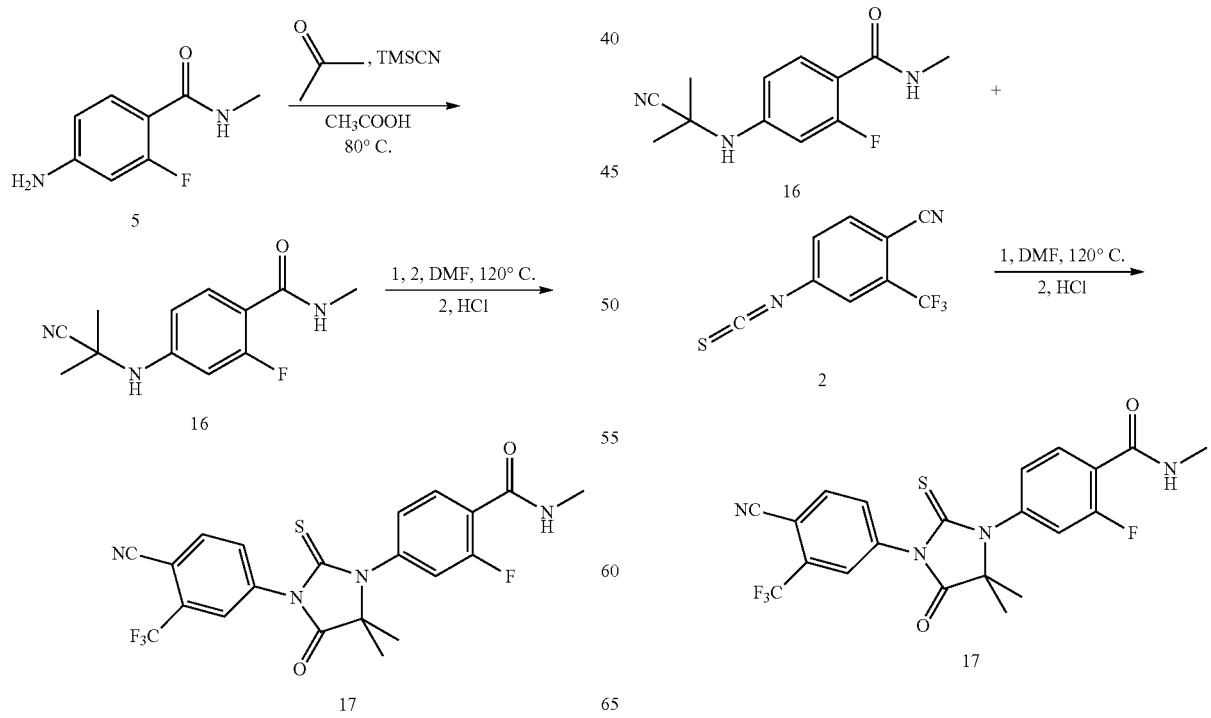

Compound 16 (1 g, 4.25 mmol) and compound 2 (1 g, 4.38 mmol) were dissolved in DMF (10 mL). The solution was heated to 120° C. and kept overnight (16 h). Ethanol (10 mL), water (10 mL) and concentrated hydrochloric acid (2 mL) were added, and the resulting mixture was heated at reflux for 1 h. The mixture was extracted with ethyl acetate, washed with brine, dried over sodium sulfate, and concentrated. The residue was purified by column chromatography (PE:EA/1:1) to give a brown solid which was further purified by preparative chromatography to give compound 17 as a white solid (337.6 mg, 17.1% yield). $^1$H NMR (DMSO, 400 MHz): δ(ppm) 8.46 (1H, s), 8.40 (1H, d, J=8.4 Hz), 8.30 (1H, s), 8.09 (1H, d, J=8 Hz) 7.79 (1H, t, J=8 Hz), 7.44 (1H, d, J=10.4 Hz), 7.34 (1H, d, J=8.0 Hz), 2.80 (3H, d, J=4 Hz), 1.96 (1H, m), 1.55 (6H, s). MS: 465.2 (M+H$^+$)

Example 5

4-{7-[4-cyano-3-(trifluoromethyl)phenyl]-5,5-dimethyl-4-oxo-2-thio-1-imidazolidinyl}-2-fluoro-N,N-dimethyl benzamide (compound 19)

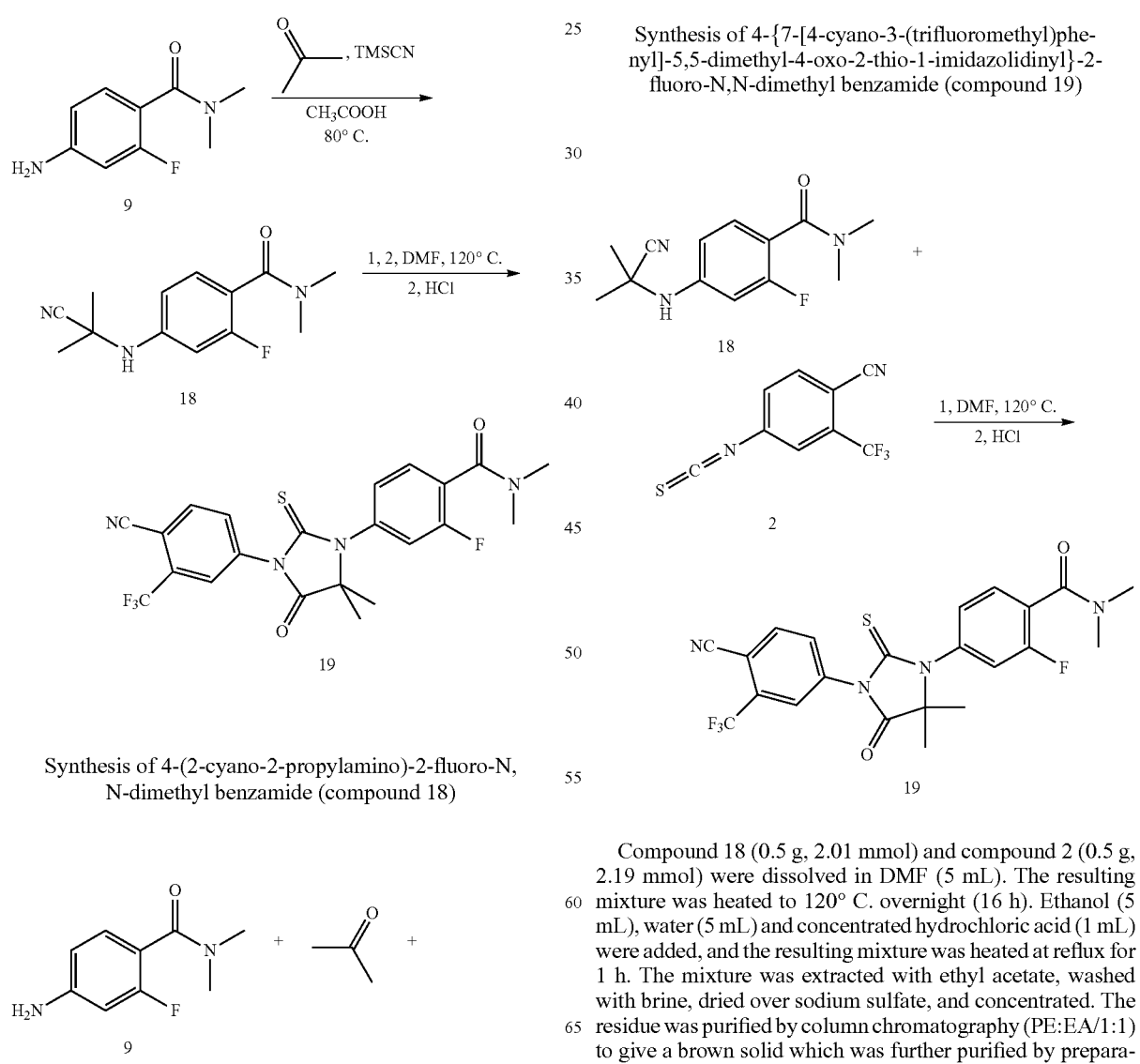

TMSCN (1.5 g, 15.12 mmol) and compound 9 (0.5 g, 2.74 mmol) were dissolved in a mixed solution of acetic acid (5 mL) and acetone (5 mL). The resulting mixture was maintained in a sealed tube at 80° C. overnight (16 h), and then cooled to room temperature. Acetone was removed under reduced pressure, water was added (10 mL), and the resulting mixture was extracted with ethyl acetate, washed with brine, dried over sodium sulfate, and concentrated. The resulting solid was washed with petroleum ether (5 mL) and dried by suction to give compound 18 as a white solid (0.55 g, 80.4% yield). $^1$H (DMSO, 400 MHz): δ(ppm) 7.20 (1H, t, J=8.4 Hz), 6.76 (1H, s), 6.67 (1H, d, J=8.8 Hz), 6.57 (1H, d, J=12.8 Hz), 2.96 (3H, s), 2.87 (3H, s), 1.66 (6H, s). MS: 250.2 (M+H$^+$).

Synthesis of 4-{7-[4-cyano-3-(trifluoromethyl)phenyl]-5,5-dimethyl-4-oxo-2-thio-1-imidazolidinyl}-2-fluoro-N,N-dimethyl benzamide (compound 19)

Compound 18 (0.5 g, 2.01 mmol) and compound 2 (0.5 g, 2.19 mmol) were dissolved in DMF (5 mL). The resulting mixture was heated to 120° C. overnight (16 h). Ethanol (5 mL), water (5 mL) and concentrated hydrochloric acid (1 mL) were added, and the resulting mixture was heated at reflux for 1 h. The mixture was extracted with ethyl acetate, washed with brine, dried over sodium sulfate, and concentrated. The residue was purified by column chromatography (PE:EA/1:1) to give a brown solid which was further purified by preparative chromatography to give compound 19 as a white solid (124.6 mg, 13% yield). $^1$H NMR (DMSO, 400 MHz): δ(ppm) 8.40 (1H, d, J=8 Hz), 8.30 (1H, s), 8.09 (1H, d, J=9.2 Hz), 7.61 (1H, t, J=8 Hz), 7.44 (1H, d, J=10.4 Hz), 7.34 (1H, d, J=7.6 Hz), 3.04 (3H, s), 2.89 (1H, s), 1.56 (6H, s). MS: 479.2 (M+H$^+$).

Example 6

4-{7-[4-cyano-3-(trifluoromethyl)phenyl]-5,5-dimethyl-4-oxo-2-thio-1-imidazolidinyl}-2-fluoro-N-trideuteromethylbenzamide (compound 21)

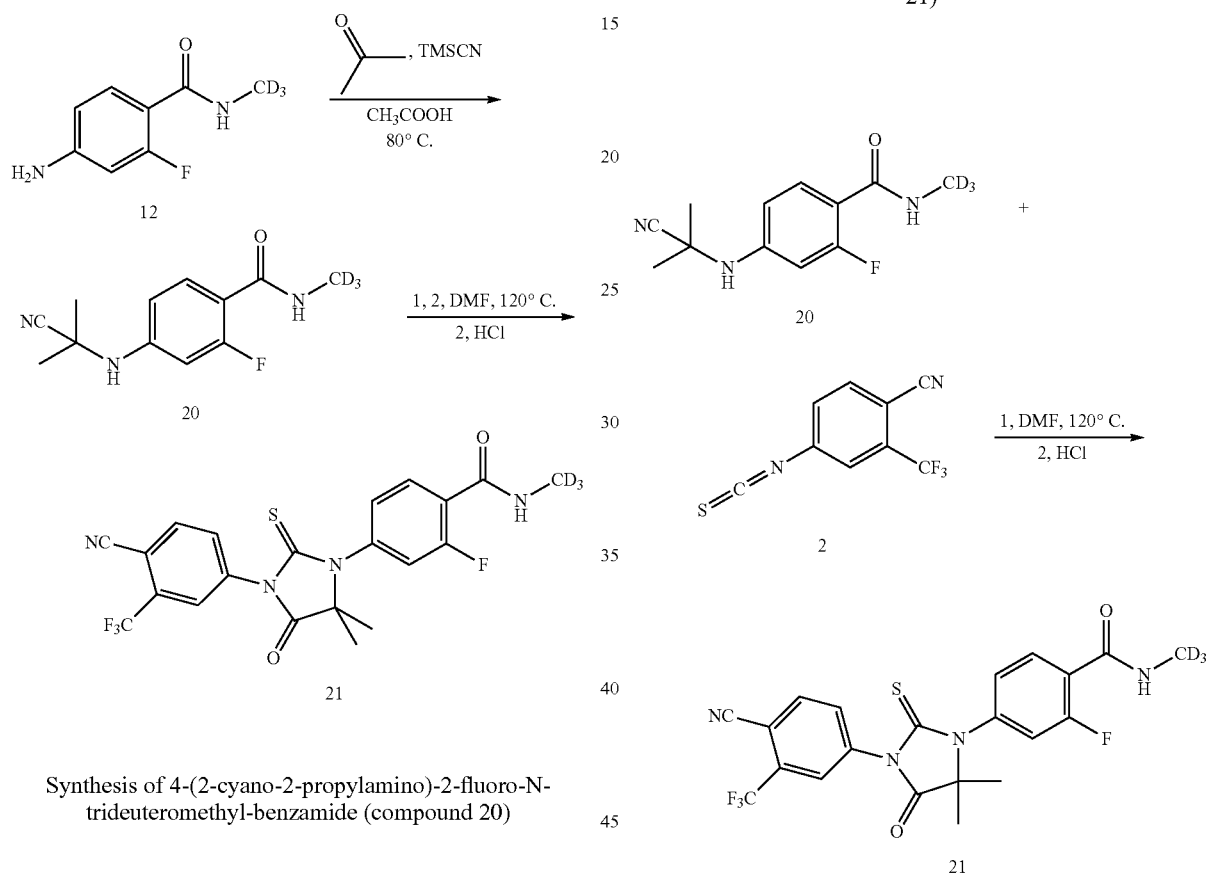

Synthesis of 4-(2-cyano-2-propylamino)-2-fluoro-N-trideuteromethyl-benzamide (compound 20)

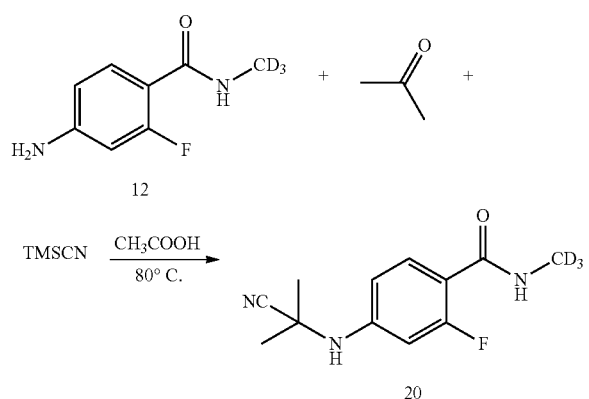

TMSCN (4 g, 40.3 mmol) and compound 12 (1.5 g, 8.76 mmol) were dissolved in a mixed solution of acetic acid (10 mL) and acetone (10 mL). The resulting mixture was maintained in a sealed tube at 80° C. overnight (16 h), and then cooled to room temperature. Acetone was removed under reduced pressure, water was added (20 mL), and the resulting mixture was extracted with ethyl acetate, washed with brine, dried over sodium sulfate, and concentrated. The resulting solid was washed with petroleum ether (10 mL) and dried by suction to give compound 20 as a white solid (1.95 g, 93.4% yield).

Synthesis of 4-{7-[4-cyano-3-(trifluoromethyl)phenyl]-5,5-dimethyl-4-oxo-2-thio-1-imidazolidinyl}-2-fluoro-N-trideuteromethyl benzamide (compound 21)

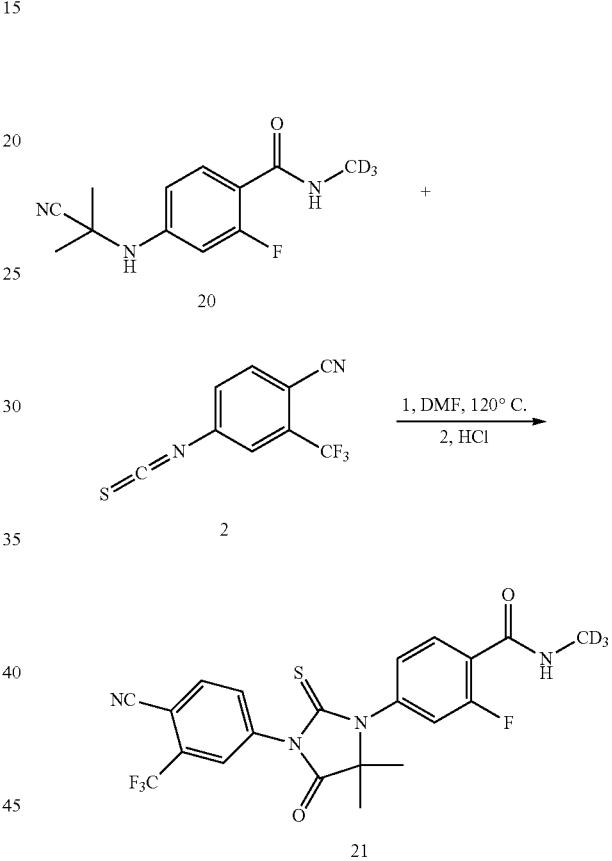

Compound 20 (0.5 g, 2.1 mmol) and compound 2 (0.5 g, 2.19 mmol) were dissolved in DMF (10 mL). The resulting mixture was heated to 120° C. overnight (16 h). Ethanol (5 mL), water (5 mL) and concentrated hydrochloric acid (1 mL) were added, and the resulting mixture was heated at reflux for 1 h. The mixture was extracted with ethyl acetate, washed with brine, dried over sodium sulfate, and concentrated. The residue was purified by column chromatography (PE:EA/1:1) to give a brown solid which was further purified by preparative chromatography to give compound 21 as a brown solid (132.7 mg, 11% yield). $^1$H NMR (DMSO, 400 MHz): δ(ppm) 8.44 (1H, s), 8.41 (1H, d, J=8.4 Hz), 8.30 (1H, s), 8.09 (1H, d, J=7.6 Hz), 7.79 (1H, t, J=8 Hz), 7.44 (1H, d, J=11.2 Hz), 7.34 (1H, d, J=8.8 Hz), 1.54 (6H, s). MS: 477.2 (M+H$^+$).

Example 7

4-{7-[4-cyano-3-(trifluoromethyl)phenyl]-5,5-dimethyl-4-oxo-2-thio-1-imidazolidinyl}-3,5-dideutero-2-fluoro-N-methyl benzamide (compound 24)

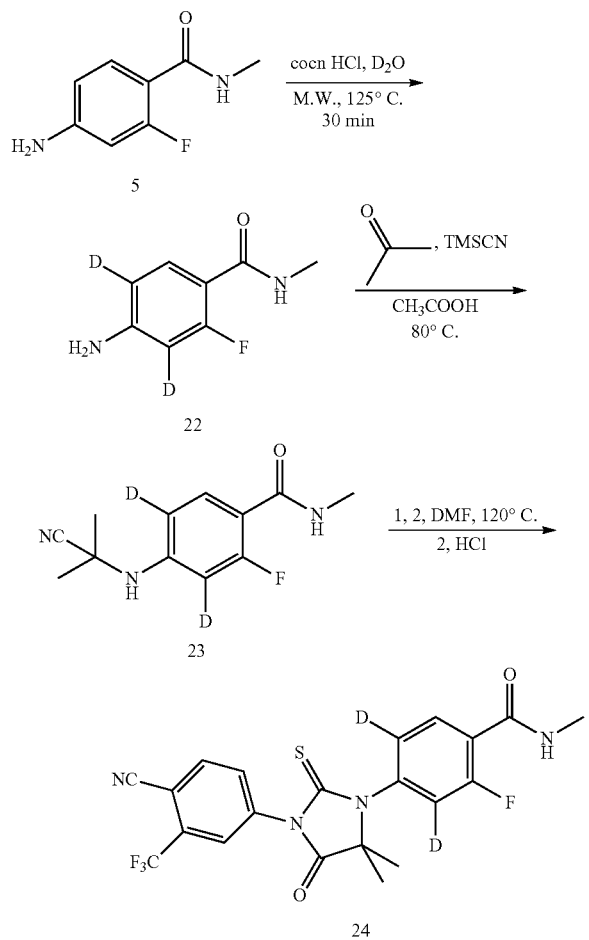

Synthesis of 3,5-dideutero-4-amino-2-fluoro-N-methyl benzamide (compound 22)

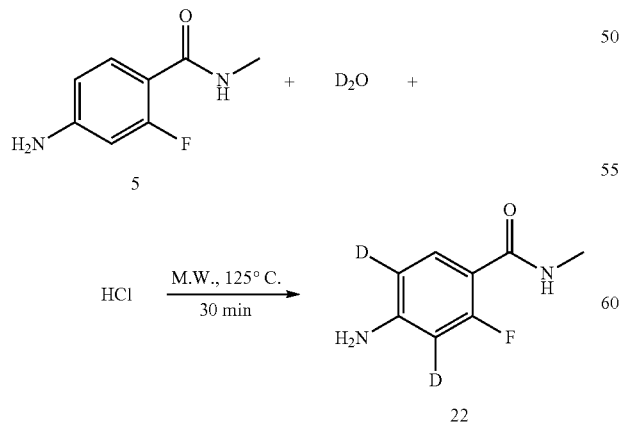

Into a suspension of compound 5 (1 g, 5.95 mmol) in heavy water (10 mL) concentrated hydrochloric acid (0.5 mL, 6.00 mmol) was added, thereby forming the heavy water solution of the hydrochloride salt of compound 5. The mixture was heated to 125° C. by microwave, and reacted for 30 min. Then the reaction solution was adjusted to alkaline with 1 M NaOH aqueous solution, and white solid precipitated. The solid was filtered and washed with water (20 mL×3), dried in an oven to give compound 22 as a white solid (0.80 g, 79.0% yield). $^1$H NMR (CDCl$_3$, 400 MHz): δ (ppm) 7.92 (1 H, d, J=8.8 Hz), 6.62 (1H, s), 4.10 (2H, s), 2.99 (3H, s).

Synthesis of 4-(2-cyano-2-propylamino)-3,5-dideutero-2-fluoro-N-methyl benzamide (compound 23)

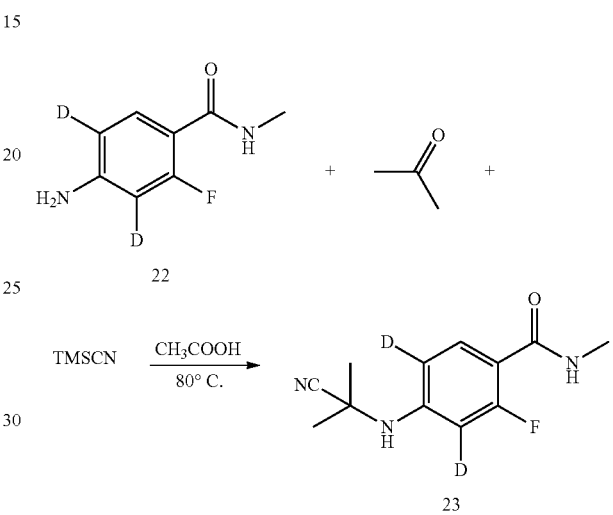

TMSCN (2 g, 20.2 mmol) and compound 22 (0.8 g, 4.5 mmol) were dissolved in a mixed solution of acetic acid (5 mL) and acetone (5 mL). The resulting mixture was maintained in a sealed tube at 80° C. overnight (16 h), and then cooled to room temperature. Acetone was removed under reduced pressure, and water was added (20 mL). The resulting mixture was extracted with ethyl acetate, washed with brine, dried over sodium sulfate, and concentrated. The resulting solid was washed with petroleum ether (10 mL) and dried by suction to give compound 23 as a white solid (1.05 g, 97.8% yield). $^1$H NMR (CDCl$_3$, 400 MHz): δ(ppm) 7.98 (1H, d, J=8.8 Hz), 6.65 (1H, s), 3.01 (3H, d, J=3.6 Hz), 1.76 (6H, s).

Synthesis of 4-{7-[4-cyano-3-(trifluoromethyl)phenyl]-5,5-dimethyl-4-oxo-2-thio-1-imidazolidinyl}-3,5-dideutero-2-fluoro-N-methyl benzamide (compound 24)

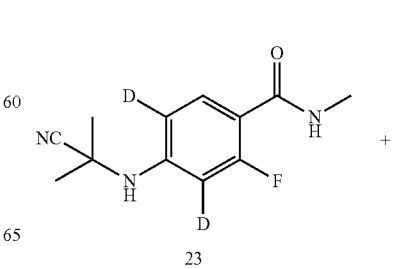

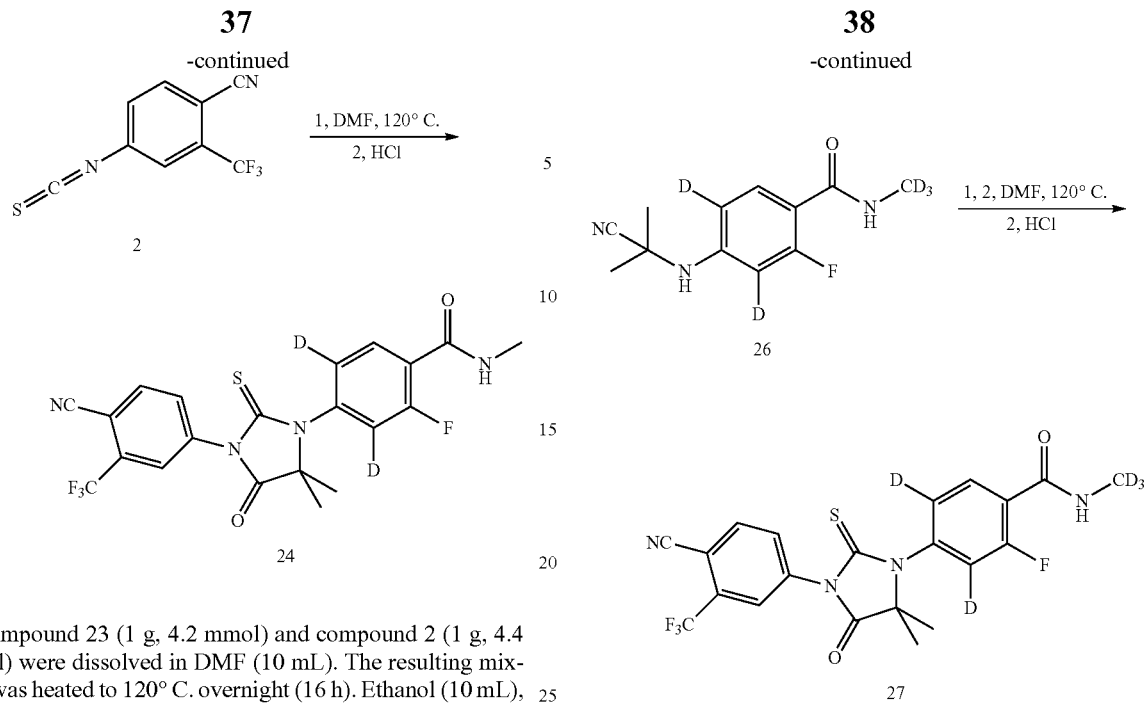

Compound 23 (1 g, 4.2 mmol) and compound 2 (1 g, 4.4 mmol) were dissolved in DMF (10 mL). The resulting mixture was heated to 120° C. overnight (16 h). Ethanol (10 mL), water (10 mL) and concentrated hydrochloric acid (2 mL) were added, and the resulting mixture was heated at reflux for 1 h. The mixture was extracted with ethyl acetate, washed with brine, dried over sodium sulfate, and concentrated. The residue was purified by column chromatography (PE:EA/1:1) to give a white solid which was further purified by preparative chromatography to give example 24 as a brown solid (210.7 mg 10.7% yield). $^1$H NMR (CDCl$_3$ 400 MHz): δ(ppm) 8.29 (1H, d J=8.4 Hz), 8.00 (1H d J=8 Hz), 7.95 (1H, s), 7.83 (1H, d J=8.4 Hz) 6.74 (1H s), 3.08 (1H d J=3.6 Hz), 1.62 (6H s) MS: 467.1 (M+H$^+$).

Example 8

4-{7-[4-cyano-3-(trifluoromethyl)phenyl]-5,5-dimethyl-4-oxo-2-thio-1-imidazolidinyl}}-3,5-dideutero-2-fluoro-N-trideuteromethyl benzamide (compound 27)

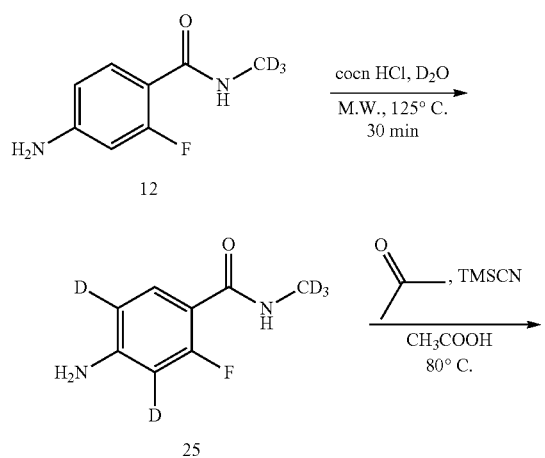

Synthesis of 3,5-dideutero-4-amino-2-fluoro-N-trideuteromethyl benzamide (Compound 25)

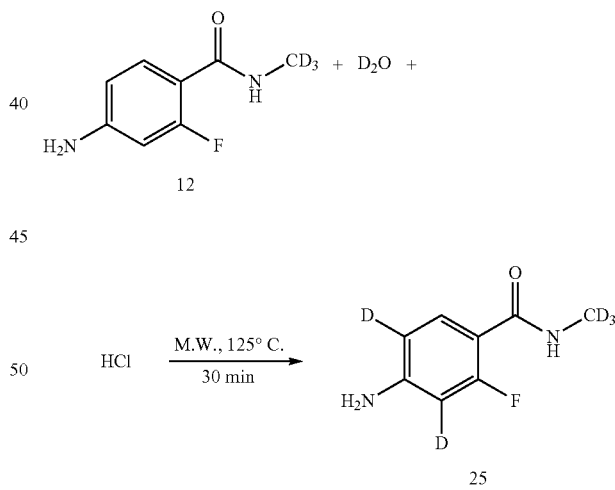

Into a suspension of compound 12 (2 g 11.68 mmol) in heavy water (10 mL) concentrated hydrochloric acid (1 mL 12.00 mmol) was added, thereby forming the heavy water solution of the hydrochloride salt of compound 12. The mixture was heated to 125° C. by microwave, and reacted for 30 min. Then the reaction solution was adjusted to alkaline with 1 M NaOH aqueous solution, white solid precipitated, and the solid was filtered and washed with water (20 mL×3), dried to give compound 22 as a white solid (1.20 g 59.3% yield). $^1$H NMR (CDCl$_3$ 400 MHz): δ (ppm) 7.92 (1H, d, J=8.8 Hz), 6.61 (1H d J=0.8 Hz), 4.12 (2H s).

Synthesis of 4-(2-cyano-2-propylamino)-3,5-dideutero-2-fluoro-N-trideuteromethyl benzamide (compound 26)

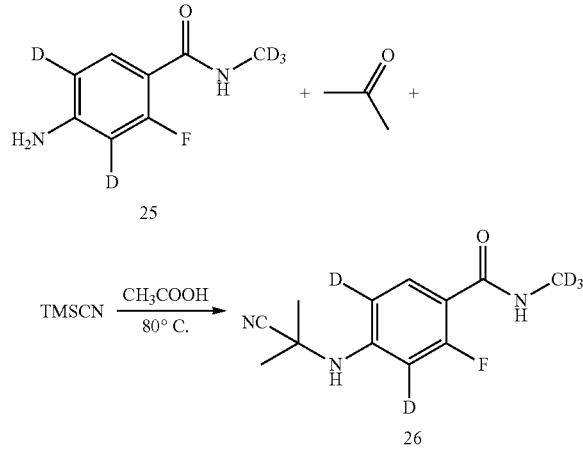

TMSCN (3.6 g 36.3 mmol) and compound 25 (1.2 g 6.2 mmol) were dissolved in a mixed solution of acetic acid (10 mL) and acetone (10 mL). The resulting mixture was maintained in a sealed tube at 80° C. overnight (16 h), and then cooled to room temperature. Acetone was removed under reduced pressure, water was added (20 mL), and the mixture was extracted with ethyl acetate, washed with brine, dried over sodium sulfate, and concentrated, The resulting solid was washed with petroleum ether (10 mL) and dried by suction to give compound 26 as a white solid (1.3 g 78.9% yield). $^1$H NMR (CDCl$_3$, 400 MHz): δ(ppm) 7.98 (1H, d J=8.8 Hz), 6.63 (1H, d, J=12 Hz), 4.35 (1H, s), 1.76 (6H s). MS: 241.1 (M+H$^+$).

Synthesis of 4-{7-[4-cyano-3-(trifluoromethyl)phenyl]-5,5-dimethyl-4-oxo-2-thio-1-imidazolidinyl}-3,5-dideutero-2-fluoro-N-methyl benzamide (compound 27)

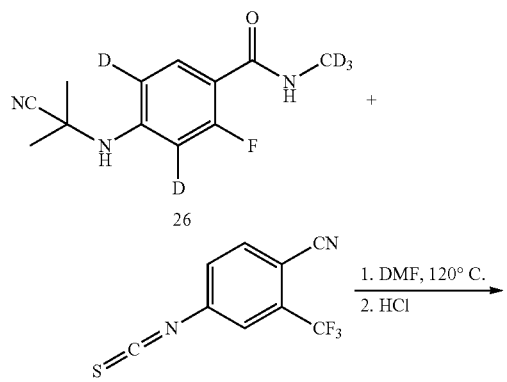

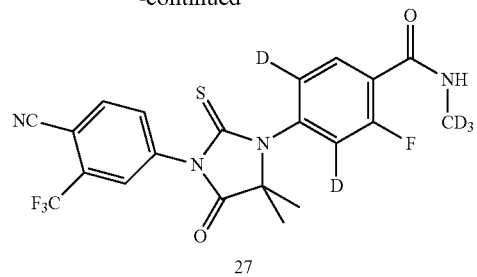

Compound 26 (0.6 g, 2.5 mmol) and compound 2 (0.6 g, 2.6 mmol) were dissolved in DMF (10 mL). The resulting mixture was heated to 120° C. and kept overnight (16 h). Ethanol (10 mL), water (10 mL) and concentrated hydrochloric acid (2 mL) were added, and the resulting mixture was heated at reflux for 1 h. The mixture was extracted with ethyl acetate, washed with brine, dried over sodium sulfate, and concentrated. The residue was purified by column chromatography (PE:EA/1:1) to give a white solid which was further purified by preparative chromatography to give example 27 as a brown solid (210.7 mg, 10.7% yield). $^1$H NMR (CDCl$_3$, 400 MHz): δ(ppm) 8.28 (1H, d, J=8.4 Hz), 8.00 (1H, d, J=8 Hz), 7.95 (1H, s), 7.83 (1H, d, J=8 Hz), 6.71 (1H, d, J=11.2 Hz), 1.62 (6H, s). MS: 470.1 (M+H$^+$).

Example 9

4-{7-[4-cyano-3-(trifluoromethyl)phenyl]-5,5-hexadeuterodimethyl-4-oxo-2-thio-1-imidazolidinyl}-2-fluoro-N-methyl benzamide (compound 29)

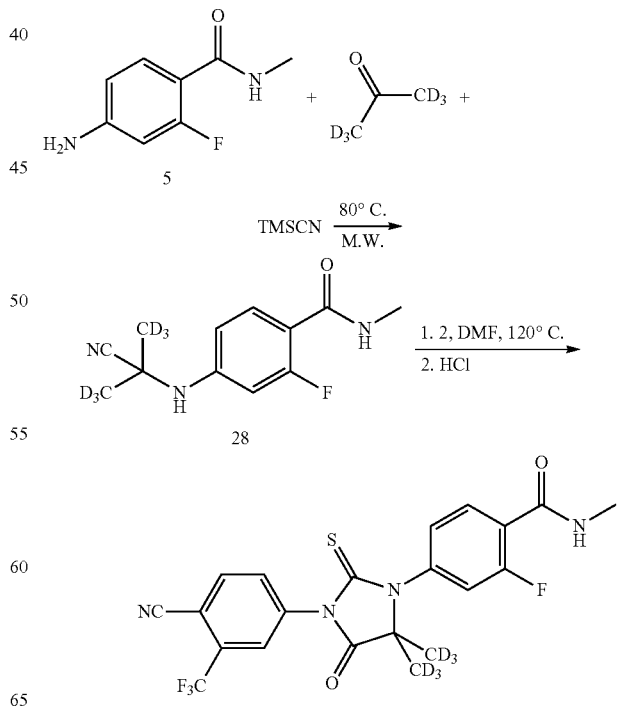

Synthesis of 4-(2-cyano-2-hexadeuteropropy-lamino)-2-fluoro-N-methyl benzamide (compound 28)

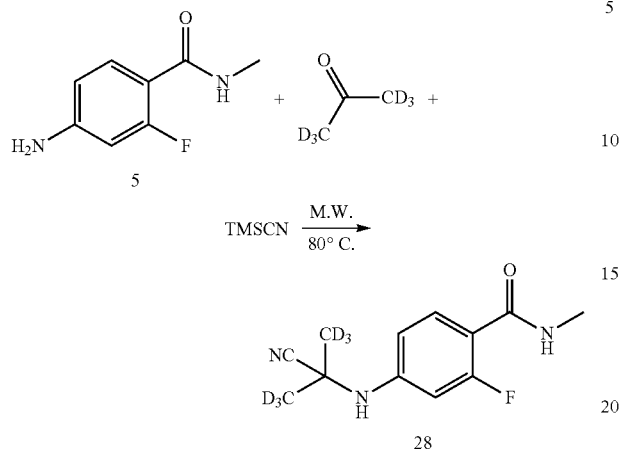

TMSCN (2.1 g, 21.2 mmol), compound 5 (0.7 g, 4.2 mmol) and deuterated acetone (1.5 g, 23.4 mmol) were placed in a microwave reaction tube, and the mixture was heated to 80° C. by microwave, and reacted for 3 h, power 50 W. The mixture was cooled to room temperature, deuterated acetone was removed under reduced pressure, and water was added (20 mL). The resulting mixture was extracted with ethyl acetate, washed with brine, dried over sodium sulfate, and concentrated. The resulting solid was washed with petroleum ether (10 mL) and dried by suction to give compound 28 as a white solid (870 mg, 86.6% yield). $^1$H NMR (CDCl$_3$, 400 MHz): δ(ppm) 7.98 (1H, t, J=8.4 Hz), 6.64 (1H, s), 6.62 (1H, d, J=4 Hz), 6.58 (1H, s), 4.37 (1H, s), 3.00 (3H, s).

Synthesis of 4-{7-[4-cyano-3-(trifluoromethyl)phe-nyl]-5,5-hexadeuterodimethyl-4-oxo-2-thio-1-imida-zolidinyl}-2-fluoro-N-methyl benzamide (compound 29)

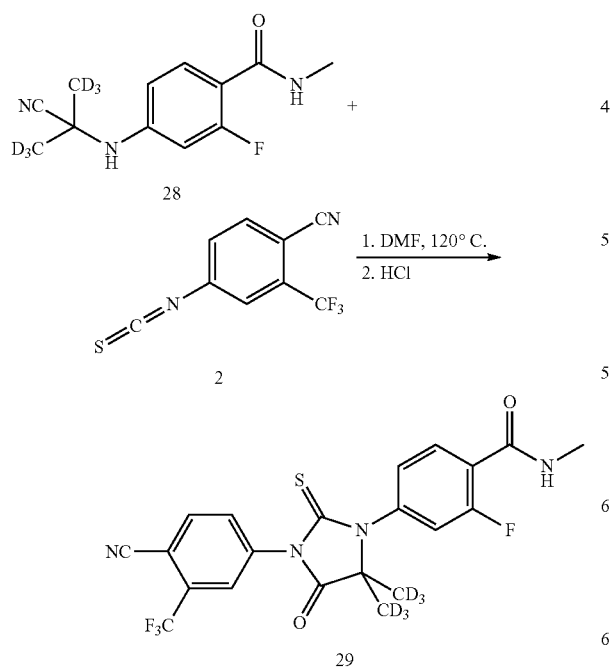

Compound 28 (630 mg, 2.6 mmol) and compound 2 (720 mg, 3.2 mmol) was dissolved in DMF (10 mL), and the resulting mixture was heated to 120° C. and kept overnight (16 h). Ethanol (10 mL), water (10 mL) and concentrated hydrochloric acid (1 mL) were added, and the resulting mixture was heated at reflux for 1 h. The mixture was extracted with ethyl acetate, washed with brine, dried over sodium sulfate, and concentrated. The residue was purified by column chromatography (PE:EA/1:1) to give a brown solid which was further purified by preparative chromatography to give example 29 as a white solid (100.4 mg, 8% yield). $^1$H NMR (CDCl$_3$, 400 MHz): δ(ppm) 8.28 (1H, t, J=8.4 Hz), 7.99 (1H, d, J=8.4 Hz), 7.95 (1H, s), 7.83 (1H, d, J=8.0 Hz), 7.25 (1H, s), 7.17 (1H, d, J=11.6 Hz) 6.81 (1H, d, J=4.8 Hz), 3.09 (3H, d, J=4.4 Hz). MS: 471.2 (M+H$^+$).

Example 10

4-{7-[4-cyano-3-(trifluoromethyl)phenyl]-5,5-hexa-deuterodimethyl-4-oxo-2-thio-1-imidazolidinyl}-2-fluoro-N-trideuteromethyl benzamide (compound 31)

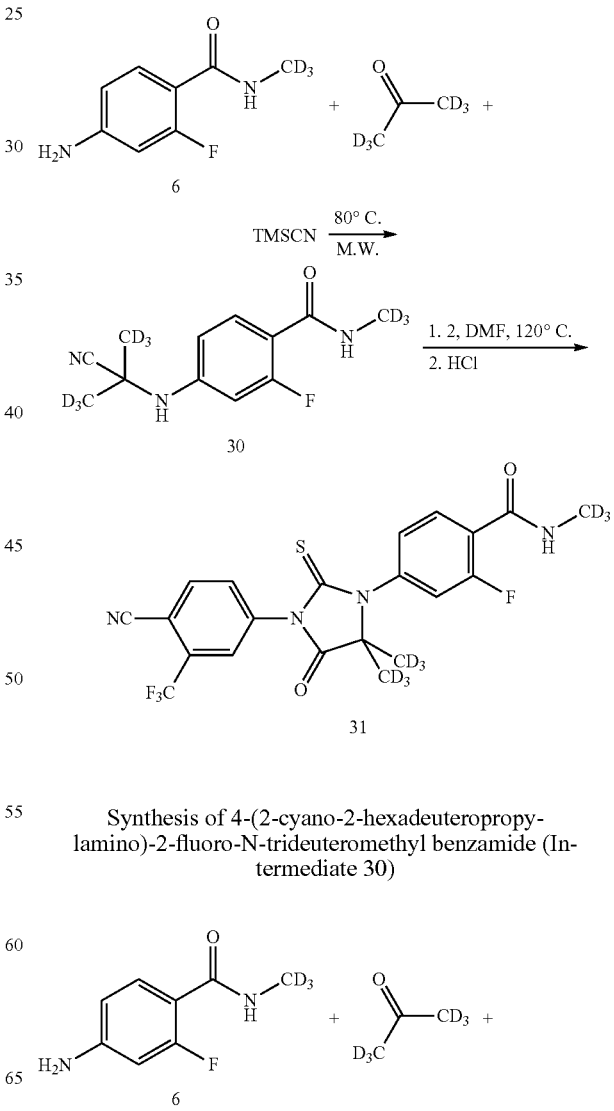

Synthesis of 4-(2-cyano-2-hexadeuteropropy-lamino)-2-fluoro-N-trideuteromethyl benzamide (Intermediate 30)

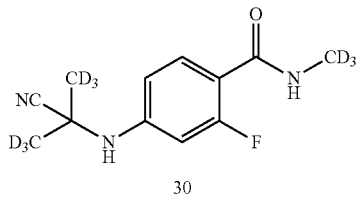

The mixture of TMSCN (1.5 g, 15.1 mmol), compound 6 (0.5 g, 3.0 mmol) and deuterated acetone (0.75 g, 11.7 mmol) was placed in a microwave reaction tube, and the mixture was heated to 80° C. by microwave, and reacted for 3 h, with power of 50 W. The mixture was cooled to room temperature, deuterated acetone was removed under reduced pressure, and water was added (20 mL). The resulting mixture was extracted with ethyl acetate, washed with brine, dried over sodium sulfate, and concentrated. The resulting solid was washed with petroleum ether (10 mL) and dried by suction to give compound 28 as a white solid (630 mg, 87.8% yield). $^1$H NMR (CDCl$_3$, 400 MHz): δ(ppm) 7.99 (1H, t, J=8.8 Hz), 6.64 (1H, s), 6.62 (1H, d, J=4 Hz), 6.58 (1H, s), 4.37 (1H, s).

Synthesis of 4-{7-[4-cyano-3-(trifluoromethyl)phenyl]-5,5-hexadeuterodimethyl-4-oxo-2-thio-1-imidazolidinyl}-2-fluoro-N-methylbenzamide (compound 31)

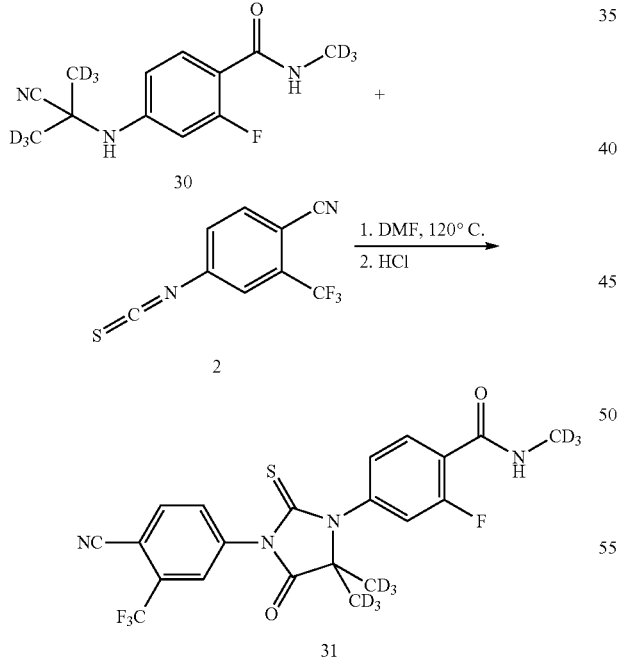

Compound 30 (630 mg, 2.6 mmol) and compound 2 (720 mg, 3.2 mmol) was dissolved in DMF (10 mL), and the resulting mixture was heated to 120° C. overnight (16 h). Ethanol (10 mL), water (10 mL) and concentrated hydrochloric acid (1 mL) were added, and the resulting mixture was heated at reflux for 1 h. The mixture was extracted with ethyl acetate, washed with brine, dried over sodium sulfate, and concentrated. The residue was purified by column chromatography (PE:EA/1:1) to give a brown solid which was further purified by preparative chromatography to give example 31 as a white solid (55.5 mg, 4.4% yield). $^1$H NMR (CDCl$_3$, 400 MHz): δ(ppm) 8.29 (1H, t, J=8.4 Hz), 8.00 (1H, d, J=8.4 Hz), 7.95 (1H, s), 7.83 (1H, d, J=8.0 Hz) 7.24 (1H, s), 7.15 (1H, d, J=12.0 Hz) 6.69 (1H, d, J=11.6 Hz). MS: 474.2 (M+H$^+$).

Example 11

4-{7-[4-cyano-3-(trifluoromethyl)phenyl]-5,5-dimethyl-4-oxo-2-thio-1-imidazolidinyl}-2-deutero-N-methyl benzamide (compound 36)

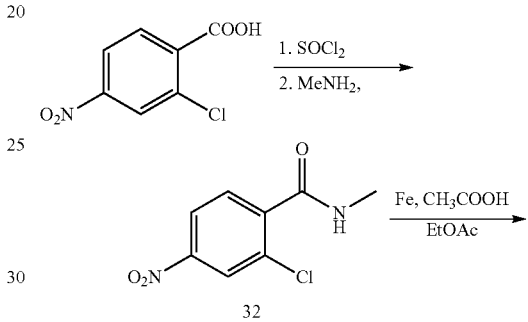

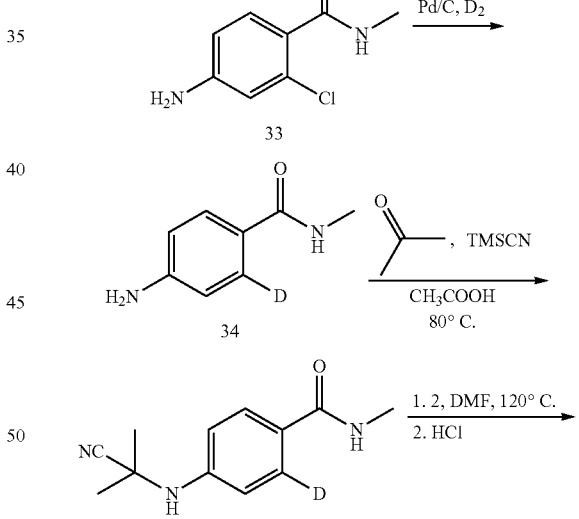

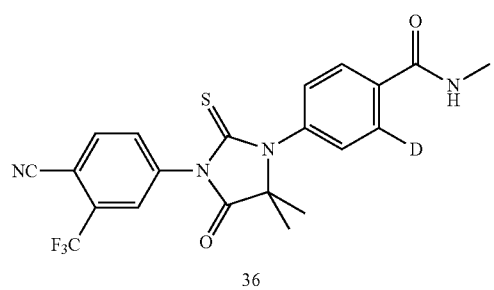

Synthesis of 2-chloro-4-nitro-N-methyl benzamide (Intermediate 32)

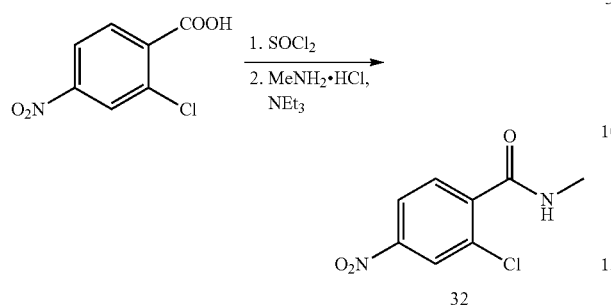

To a solution of 4-nitro-2-chloro-benzoic acid (9.0 g, 44.6 mmol) in thionyl chloride (100 mL) 4 drops of DMF were added, and the reaction mixture was heated at reflux for one hour and cooled to room temperature. The solvent was removed under reduced pressure to give a pale yellow solid. The solid was dissolved in dichloromethane (50 mL). Into a solution of methylamine hydrochloride (3.0 g, 44.6 mmol) in dichloromethane (50 mL) triethylamine (13 mL, 89.3 mmol) was added, thereby obtaining a white suspension. After stirred at room temperature for half an hour, the suspension was added to the above dichloromethane solution slowly, and the resulting mixture was maintained at room temperature for one hour. The mixture was filtered to give a white solid, which was washed successively with water and dichloromethane (5 mL×2) twice to give the intermediate 32 (6.3 g, 65.8% yield).

Synthesis of 2-chloro-4-amino-N-methyl benzamide (Intermediate 33)

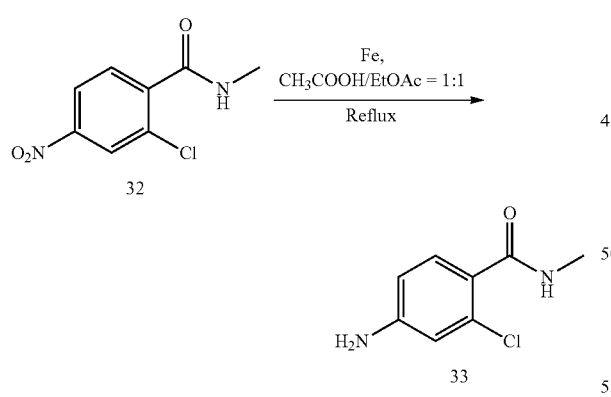

Compound 32 (6.3 g, 29.1 mmol) was dissolved in a solution of ethyl acetate and acetic acid (50 mL+25 mL). 17 g of iron powder was added, and the resulting mixture was refluxed overnight (16 h). The mixture was cooled to room temperature. The solid was filtered, and washed with ethyl acetate (3×50 mL) for three times. The organic phases were combined, washed with brine, dried over sodium sulfate, and concentrated to give a yellow solid which was purified by column chromatography (DCM:McOH=50:1) to give compound 33 as a pale yellow solid (3.4 g, 62.0% yield).

Synthesis of 2-deutero-4-amino-N-methyl benzamide (Intermediate 33)

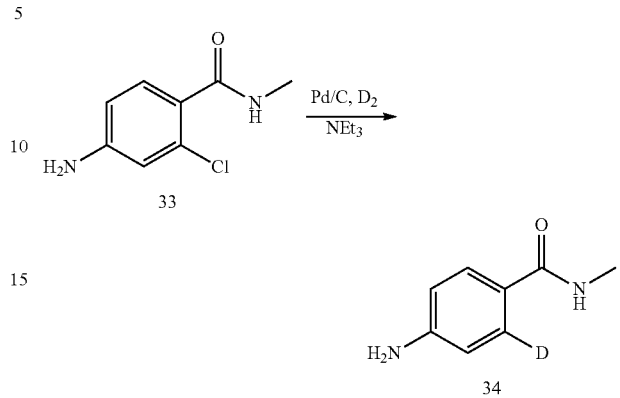

500 mg of Pd/C and 20 mL of heavy water were added into a 250 mL round bottom flask, hydrogen was filled into the flask, and the resulting mixture was stirred at room temperature for 3 days. Then a solution of compound 33 (560 mg, 3.0 mmol) in ethyl acetate (10 mL) and triethylamine (303 mg, 3.0 mmol) were added, and the resulting mixture was stirred for 2 h. The mixture was filtered, and the resulting solid was washed with ethyl acetate (20 mL×3) for three times. Layers were separated, and the organic phase was washed with water (20 mL×2), dried over anhydrous sodium sulfate, and filtered. The solvent was evaporated to give a white solid 34 (368 mg, 81.2% yield). $^1$H NMR (DMSO, 400 MHz): δ(ppm) 7.82 (1H, d, J=6.8 Hz), 7.19 (2H, s), 2.77 (3H, s).

Synthesis of 4-(2-cyano-2-propylamino)-2-deuteron-N-methyl benzamide (Intermediate 35)

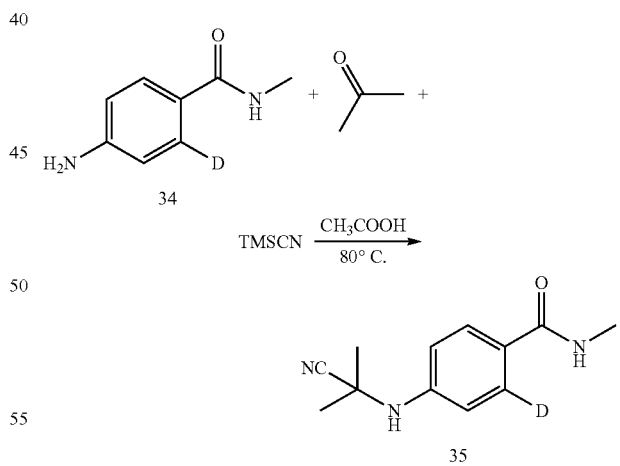

TMSCN (1 g, 5.9 mmol) and compound 5 (368 mg, 2.4 mmol) were dissolved in a mixed solution of acetic acid (5 mL) and acetone (5 mL). The resulting mixture was placed in a sealed tube for reacting at 80° C. overnight (16 h), and then cooled to room temperature. Acetone was removed under reduced pressure, water was added (10 mL), and the resulting mixture was extracted with ethyl acetate, washed with brine, dried over sodium sulfate, and concentrated, The resulting solid was washed with petroleum ether (10 mL) and dried by suction to give compound 35 as a white solid (476 g, 90.9% yield). $^1$H NMR (DMSO, 400 MHz): δ(ppm) 8.12 (1H, s), 7.69 (1H, d, J=8.8 Hz), 6.81 (2H, s), 6.59 (1H, s), 2.74 (3H, s), 1.67 (6H, s).

Synthesis of 4-{7-[4-cyano-3-(trifluoromethyl)phenyl]-5,5-dimethyl-4-oxo-2-thio-1-imidazolidinyl}-2-deutero-N-methyl benzamide (compound 36)

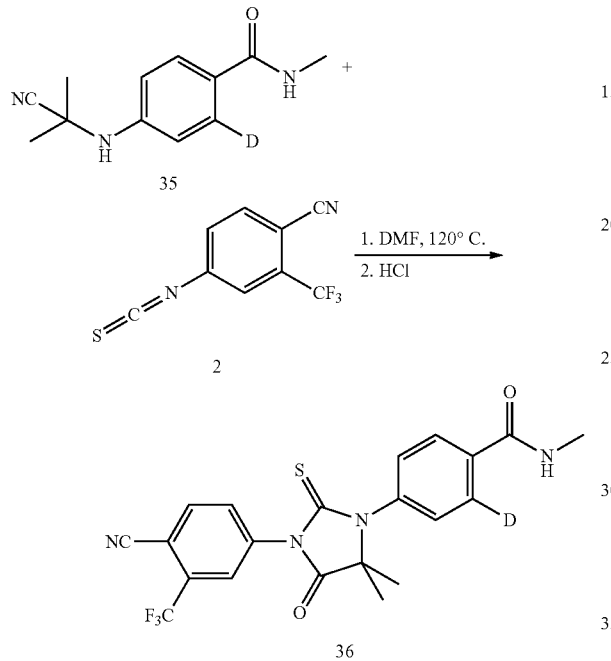

Compound 35 (476 mg, 2.2 mmol) and compound 2 (600 mg, 2.6 mmol) were dissolved in DMF (10 mL), and the resulting mixture was heated to 120° C. and kept overnight (16 h). Ethanol (10 mL), water (10 mL) and concentrated hydrochloric acid (1 mL) were added, and the resulting mixture was heated at reflux for 1 h. The mixture was extracted with ethyl acetate, washed with brine, dried over sodium sulfate, and concentrated. The residue was purified by column chromatography (PE:EA/1:1) to give a brown solid which was further purified by preparative chromatography to give example 36 as a white solid (92.1 mg, 9.4% yield). $^1$H NMR (CDCl$_3$, 400 MHz): δ(ppm) 7.99 (1H, d, J=8.8 Hz), 7.96 (1H, s), 7.92 (1H, d, J=8.8 Hz), 7.84 (1H, d, J=8 Hz), 7.39 (2H, s), 6.18 (1H, s), 3.05 (3H, d, J=4.4 Hz), 1.60 (6H, s). MS: 448.2 (M+H$^+$).

Example 12

4-{7-[4-cyano-3-(trifluoromethyl)phenyl]-5,5-dimethyl-4-oxo-2-thio-1-imidazolidinyl}-2-deutero-N-trideuteromethyl benzamide (compound 41)

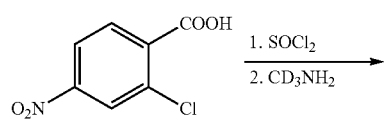

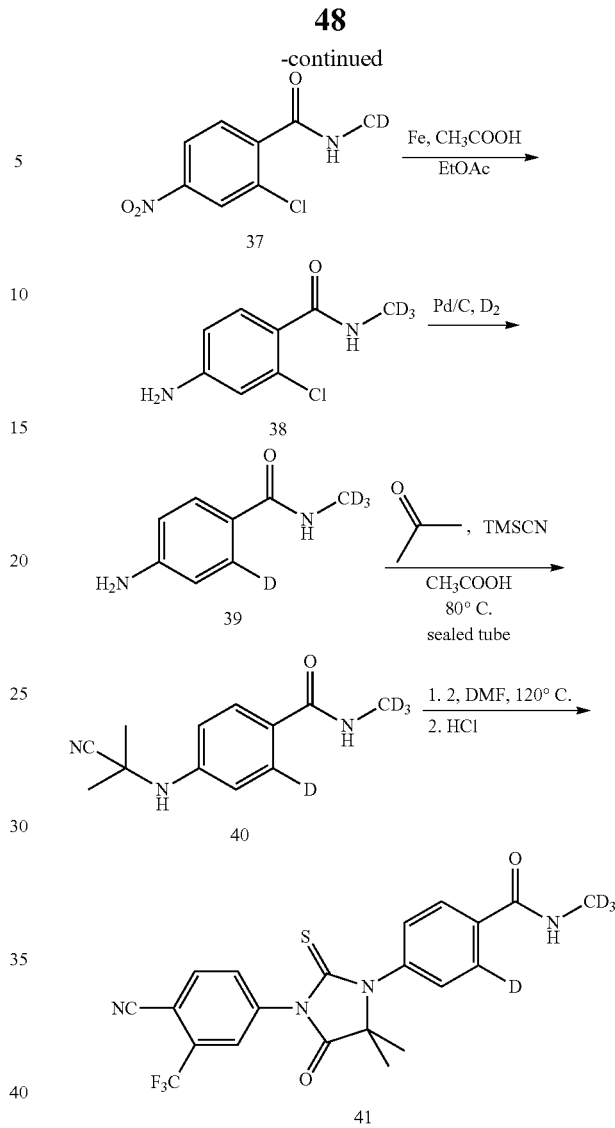

Synthesis of 2-chloro-4-nitro-N-trideuteromethyl benzamide (Intermediate 37)

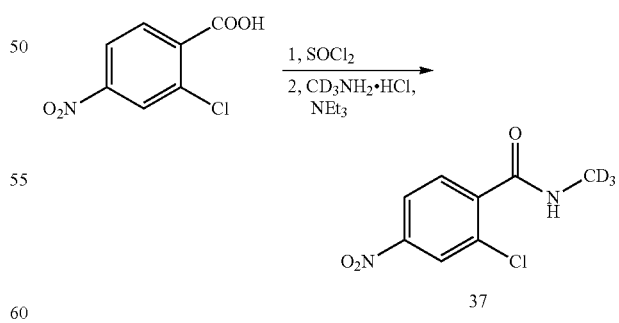

Into a solution of 4-nitro-2-chloro benzoic acid (3.0 g, 14.9 mmol) in thionyl chloride (50 mL) 4 drops of DMF were added. The reaction mixture was heated at reflux for one hour, and cooled to room temperature. The solvent was removed under reduced pressure to give a pale yellow solid. The solid was dissolved in dichloromethane (20 mL). Triethylamine (2.3 g, 22.8 mmol) was added into a solution of deuterated methylamine hydrochloride (1.0 g, 14.9 mmol) in methylene chloride (10 mL), thereby obtaining a white suspension. After stirred at room temperature for half an hour, the suspension solution was added to the above methylene chloride solution slowly, the resulting mixture was maintained at room temperature for reacting for one hour. The resulting mixture was filtered to give a white solid, which was washed successively with water and dichloromethane (5 mL×2) twice, thereby obtaining the intermediate 37 (2.8 g, 86.6% yield).

Synthesis of 2-chloro-4-amino-N-trideuteromethyl benzamide (Intermediate 38)

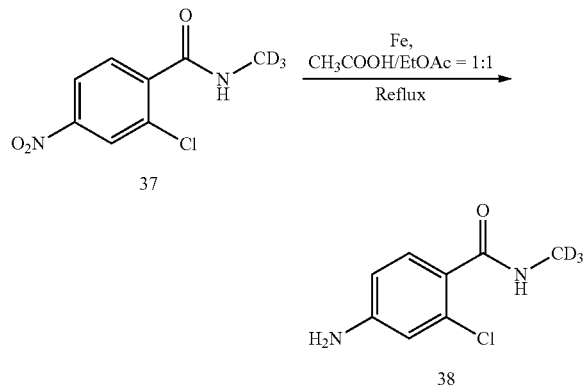

Compound 37 (1.2 g, 5.5 mmol) was dissolved in a solution of ethyl acetate and acetic acid (10 mL+10 mL). 3 g of iron powder was added, the resulting mixture was refluxed overnight (16 h), and then the mixture was cooled to room temperature. The solid was filtered, and washed with ethyl acetate (3×10 mL) for three times. The organic phases were combined, washed with brine, dried over sodium sulfate, and concentrated to give a yellow solid which was purified by column chromatography (DCM:MeOH=50:1) to give compound 38 as a pale yellow solid (650 mg, 76.7% yield).

Synthesis of 2-deutero-4-amino-N-trideuteromethyl benzamide (Intermediate 39)

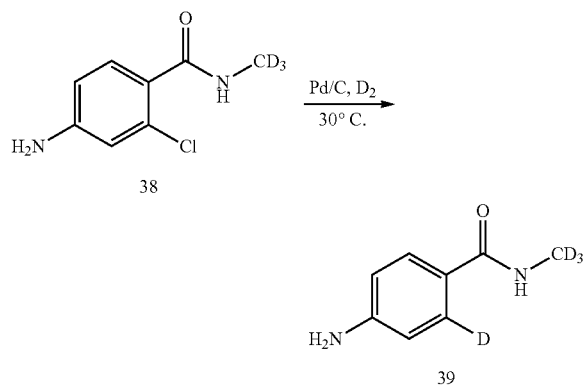

500 mg Pd/C and 20 mL of heavy water were added into a 250 mL round bottom flask, and hydrogen was filled to the flask. The mixture was stirred at room temperature for 3 days.

Then a solution of compound 38 (650 mg, 3.5 mmol) in ethyl acetate (10 mL) and triethylamine (354 mg, 3.5 mmol) were added to the reaction system, the resulting mixture was stirred for 2 hours. The resulting solid was filtered, and washed with ethyl acetate (20 mL×3) for three times. Layers were separated, and the organic phase was washed with water (20 mL×2), dried over anhydrous sodium sulfate, and filtered. The solvent was evaporated to give a white solid 39 (500 mg, $^1$H NMR (DMSO, 400 MHz): δ (ppm) 7.82 (1H, d, J=6.8 Hz), 7.19 (2H, s).

Synthesis of 4-(2-cyano-2-propylamino)-2-deutero-N-trideuteromethyl benzamide (Intermediate 40)

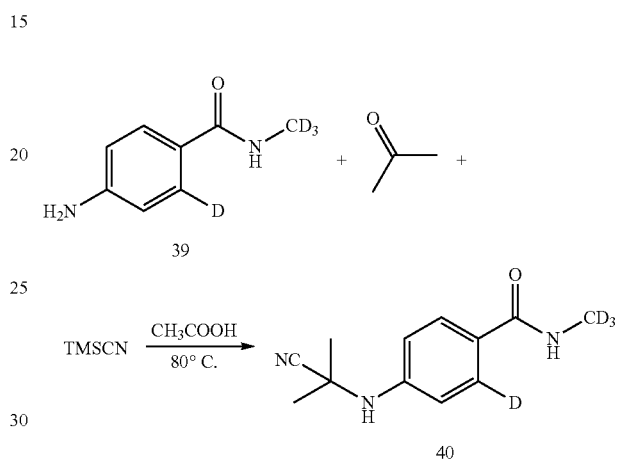

TMSCN (1.5 g, 15.1 mmol) and compound 39 (500 mg, 3.2 mmol) were dissolved in a mixed solution of acetic acid (5 mL) and acetone (5 mL). The resulting mixture was placed in a sealed tube at 80° C. for reacting overnight (16 h), and then cooled to room temperature. Acetone was removed under reduced pressure, water was added (20 mL), and the resulting mixture was extracted with ethyl acetate, washed with brine, dried over sodium sulfate, and concentrated. The resulting solid was washed with petroleum ether (10 mL) and filtered to give compound 40 as a white solid (564 mg, 79.8% yield).

Synthesis of 4-{7-[4-cyano-3-(trifluoromethyl)phenyl]-5,5-dimethyl-4-oxo-2-thio-1-imidazolidinyl}-2-deutero-N-trideuteromethyl benzamide (compound 41)

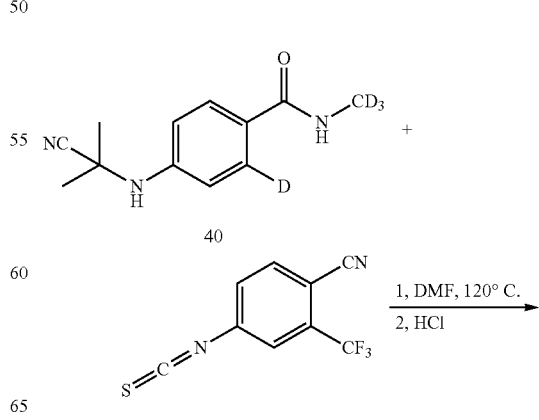

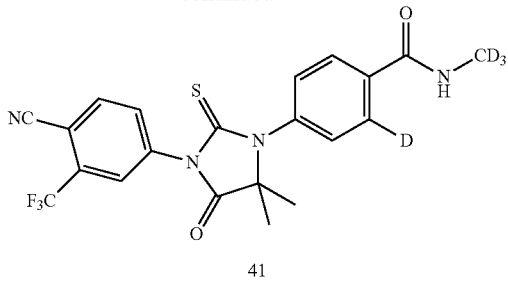

41

Compound 40 (564 mg, 2.6 mmol) and compound 2 (600 mg, 2.6 mmol) were dissolved in DMF (10 mL), the resulting mixture was heated to 120° C. overnight (16 h). Ethanol (10 mL), water (10 mL) and concentrated hydrochloric acid (1 mL) were added, and the resulting mixture was heated at reflux for 1 h. The mixture was extracted with ethyl acetate, washed with brine, dried over sodium sulfate, and concentrated. The residue was purified by column chromatography (PE:EA/1:1) to give a brown solid which was further purified by preparative chromatography to give example 41 as a white solid (107 mg 9.1% yield). $^1$H NMR (CDCl$_3$ 400 MHz): δ(ppm) 7.99 (1H, d, J=8.4 Hz), 7.96 (1H, s), 7.92 (1H, d J=8.8 Hz), 7.84 (1H, d, J=8.4 Hz), 7.39 (2H, s), 6.14 (1H, s), 1.58 (6H, s), MS: 451.2 (M+H$^+$).

Example 13

4-{7-[4-cyano-3-trifluoromethyl-2,6-dideuterophenyl]-5,5-dimethyl-4-oxo-2-thio-1-imidazolidinyl}-2-fluoro-N-methyl benzamide (compound 44)

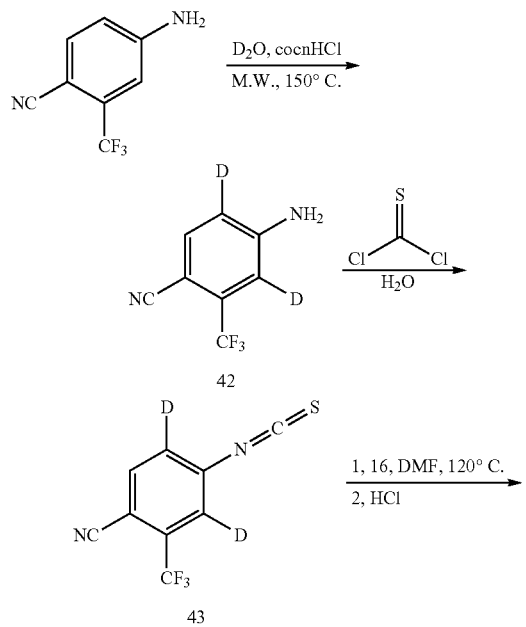

Synthesis of 4-amino-2-trifluoromethyl-3,5-dideuterobenzonitrile (Intermediate 42)

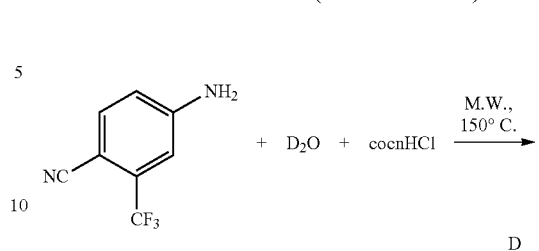

Into a suspension of 4-amino-2-trifluoromethyl benzonitrile (1 g, 5.4 mmol) in heavy water (15 mL) concentrated hydrochloric acid (cocn HCl, 0.45 mL, 5.40 mmol) was added. The mixture was heated to 150° C. by microwave, and maintained for 3 h. Ethyl acetate (20 mL) was added into the reaction mixture, and then the mixture was adjusted to alkaline with 1 M NaOH solution. Layers were separated, the aqueous phase was extracted with ethyl acetate (20 mL×2) twice, and the organic phases were combined, dried over anhydrous sodium sulfate, and filtered. The solvent was removed under reduced pressure to give compound 42 as a white solid (960 mg, 95% yield). $^1$H NMR (CDCl$_3$, 400 MHz): δ (ppm) 7.56 (1H, s), 4.41 (2H, s).

Synthesis of 4-isothiocyanato-2-trifluoromethyl-3,5-dideuterobenzonitrile (Intermediate 43)

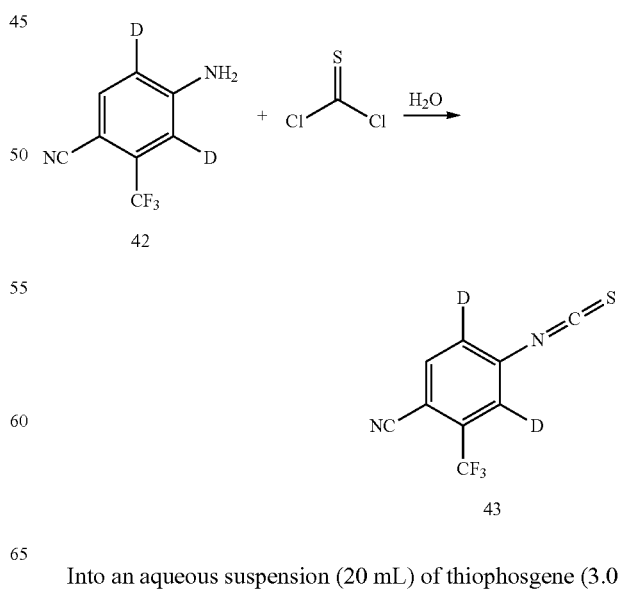

Into an aqueous suspension (20 mL) of thiophosgene (3.0 g, 26.2 mmol) 42 (960 mg, 5.1 mmol) was slowly added in

53 batches. After the reaction mixture was stirred at room temperature (20° C.) for one hour, it was extracted with ethyl acetate (3×20 mL) for three times. The organic layers were combined and washed with saturated brine (20 mL) once, dried (Na₂SO₄), filtered, and concentrated under reduced pressure to give a black solid, which was purified by column chromatography to give 43 as a white solid (1.1 g, 92% yield).

Synthesis of 4-{7-[4-cyano-3-trifluoromethyl-2,6-dideuterophenyl]-5,5-dimethyl-4-oxo-2-thio-1-imidazolidinyl}-2-fluoro-N-methylbenzamide (compound 44)

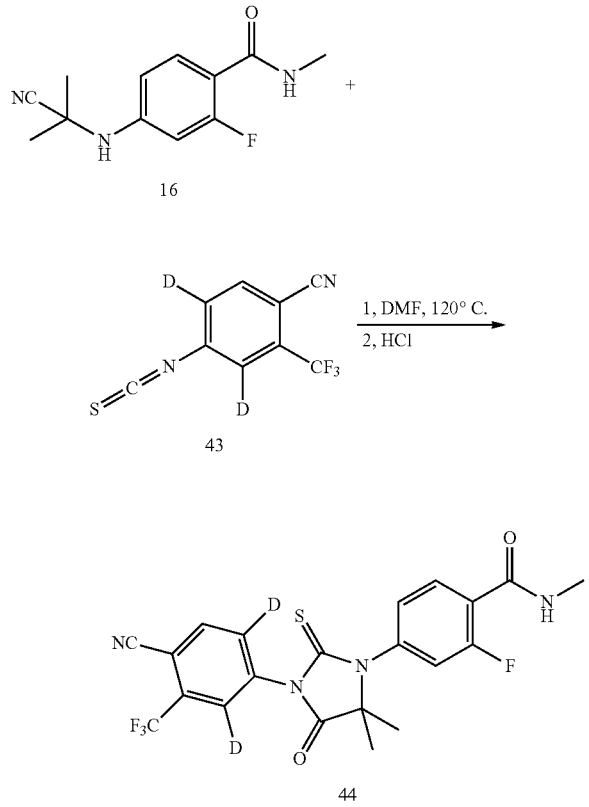

Compound 16 (0.6 g, 2.6 mmol) and compound 43 (0.5 g, 2.2 mmol) were dissolved in DMF (10 mL). The resulting solution was heated to 125° C. and kept overnight (16 h). Ethanol (10 mL), water (10 mL) and concentrated hydrochloric acid (2 mL) were added, and the resulting mixture was heated at reflux for 1 h. The mixture was extracted with ethyl acetate, washed with brine, dried over sodium sulfate, and concentrated. The residue was purified by column chromatography (PE:EA/1:1) to give a brown solid which was further purified by preparative chromatography to give example 44 as a white solid (47.1 mg, 4% yield). ¹H NMR (CDCl₃, 400 MHz): δ(ppm) 7.99 (1H, d, J=8.8 Hz), 7.96 (1H, s), 7.92 (1H, d, 8.8 Hz), 7.84 (1H, d, J=8.4 Hz), 7.39 (2H, s), 6.18 (1H, s), 3.05 (3H, d, J=4.4 Hz), 1.60 (6H, s). MS: 467.2 (M+H⁺).

54

Example 14

4-{7-[4-cyano-3-trifluoromethyl-2,6-dideuterophenyl]-5,5-dimethyl-4-oxo-2-thio-1-imidazolidinyl}-2-fluoro-N-trideuteromethyl benzamide (compound 45)

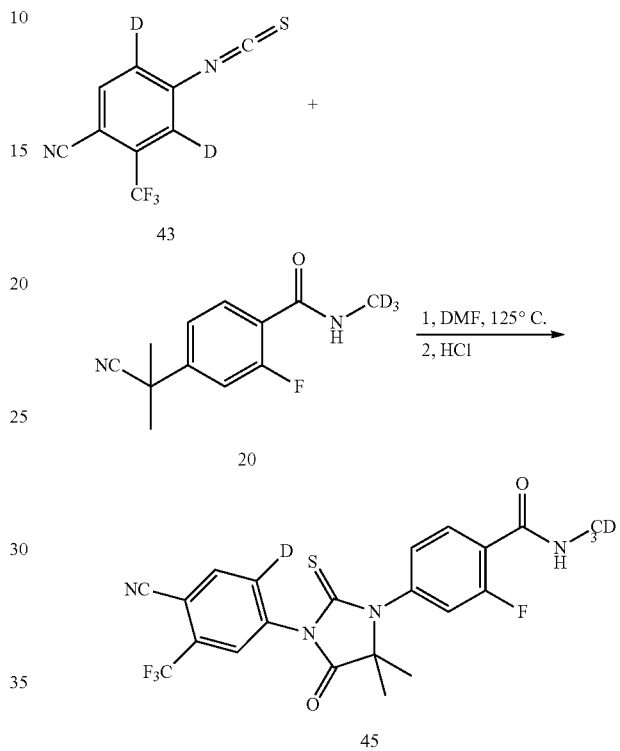

Compound 20 (0.6 g, 2.7 mmol) and compound 43 (0.5 g, 2.2 mmol) were dissolved in DMF (10 mL). The resulting solution was heated to 125° C. overnight (16 h). Ethanol (10 mL), water (10 mL) and concentrated hydrochloric acid (2 mL) were added, and the resulting mixture was heated at reflux for 1 h. The mixture was extracted with ethyl acetate, washed with brine, dried over sodium sulfate, and concentrated. The residue was purified by column chromatography (PE:EA/1:1) to give a brown solid which was further purified by preparative chromatography to give example 44 as a white solid (62.0 mg, 6.8% yield). ¹H NMR (CDCl₃, 400 MHz): δ(ppm) 7.99 (1H, d, J=8.4 Hz), 7.96 (1H, s), 7.92 (1H, d, 8.8 Hz), 7.84 (1H, d, J=8.4 Hz), 7.39 (2H, s), 6.14 (1H, s), 1.60 (6H, s). MS: 470.2 (M+H⁺).

Example 15

The following Examples are similar to the method of Example 1, except that methylamine hydrochloride is replaced by CHD₂NH₂ or CH₂DNH₂ or CD₃NH₂ hydrochloride, cyclobutanone is replaced by hexadeuterated acetone (CD₃COCD₃) or acetone, 4-amino-2-trifluoromethylbenzonitrile is replaced by deuterated 4-amino-2-trifluoromethylbenzonitrile, and 2-fluoro-N-methyl-4-amino-benzamide is replaced by deuterated N-methyl-4-amino-benzamide. The compounds prepared were shown in Table 1.

TABLE 1

| No. | structure | Name |
|-----|-----------|------|
| 46 | 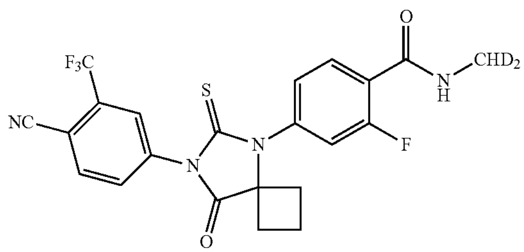 | 4-[7-(2-trifluoromethyl-4-cyanophenyl)-8-oxo-6-thio-5,7-diazaspiro[3,4]-5-octyl]-2-fluoro-N-(dideuteromethyl)benzamide |
| 47 | 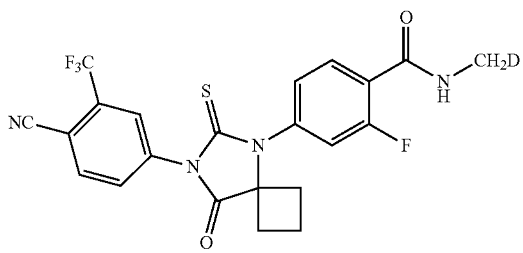 | 4-[7-(2-trifluoromethyl-4-cyanophenyl)-8-oxo-6-thio-5,7-diazaspiro[3,4]-5-octyl]-2-fluoro-N-(deuteromethyl)benzamide |
| 48 | 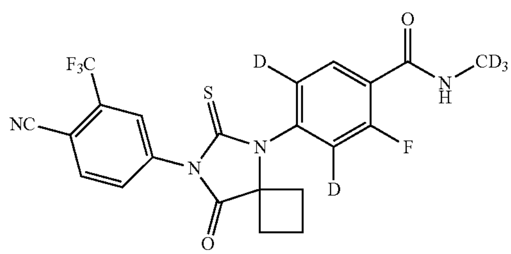 [SMILES: [2H]c1cc(C(=O)NC([2H])([2H])[2H])c(F)c([2H])c1N1C(=S)N(c2ccc(C#N)c(C(F)(F)F)c2)C(=O)C12CCC2] | 4-[7-(2-trifluoromethyl-4-cyanophenyl)-8-oxo-6-thio-5,7-diazaspiro[3,4]-5-octyl]-2-fluoro-3,5-dideutero-N-(trideuteromethyl)benzamide |
| 49 | 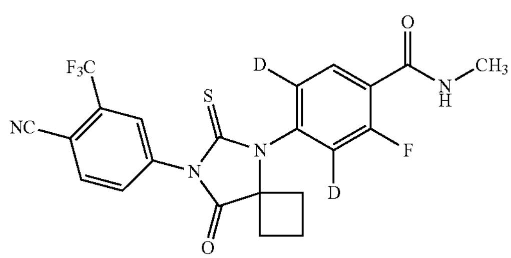 | 4-[7-(2-trifluoromethyl-4-cyanophenyl)-8-oxo-6-thio-5,7-diazaspiro[3,4]-5-octyl]-2-fluoro-3,5-dideutero-N-methylbenzamide |
| 50 | 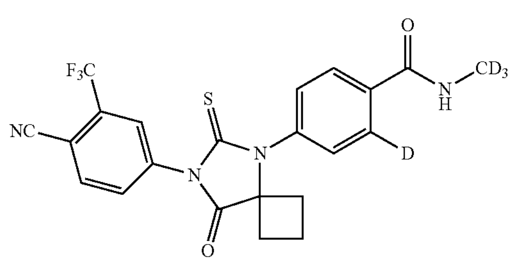 [SMILES: [2H]c1cc(N2C(=S)N(c3ccc(C#N)c(C(F)(F)F)c3)C(=O)C23CCC3)ccc1C(=O)NC([2H])([2H])[2H]] | 4-[7-(2-trifluoromethyl-4-cyanophenyl)-8-oxo-6-thio-5,7-diazaspiro[3,4]-5-octyl]-2-dideutero-N-(trideuteromethyl)benzamide |
| 51 | 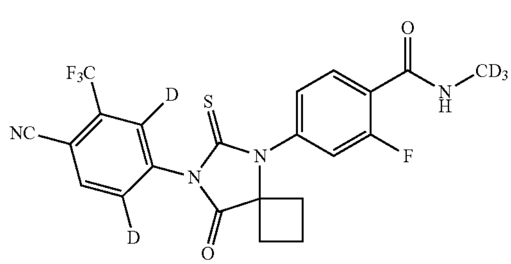 | 4-[7-(2-trifluoromethyl-4-cyano-2,6-dideuterophenyl)-8-oxo-6-thio-5,7-diazaspiro[3,4]-5-octyl]-2-fluoro-N-(trideuteromethyl)benzamide |

TABLE 1-continued

| No. | structure | Name |
|---|---|---|
| 52 | 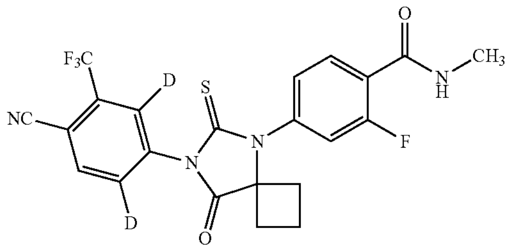 [SMILES: [2H]c1cc(C#N)c(C(F)(F)F)c([2H])c1N1C(=O)C2(CCC2)N(c2ccc(C(=O)NC([2H])([2H])[2H])c(F)c2)C1=S] | 4-[7-(2-trifluoromethyl-4-cyano-2,6-dideuterophenyl)-8-oxo-6-thio-5,7-diazaspiro[3,4]-5-octyl]-2-fluoro-N-methylbenzamide |
| 53 | 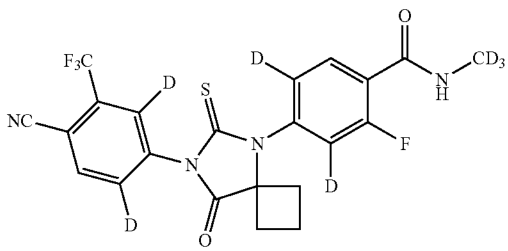 | 4-[7-(2-trifluoromethyl-4-cyano-2,6-dideuterophenyl)-8-oxo-6-thio-5,7-diazaspiro[3,4]-5-octyl]-2-fluoro-3,5-dideutero-N-(trideuteromethyl)benzamide |
| 54 | 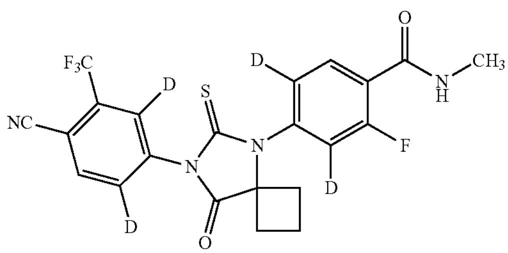 [SMILES: [2H]c1cc(C#N)c(C(F)(F)F)c([2H])c1N1C(=O)C2(CCC2)N(c2c([2H])cc(C(=O)NC([2H])([2H])[2H])c(F)c2[2H])C1=S] | 4-[7-(2-trifluoromethyl-4-cyano-2,6-dideuterophenyl)-8-oxo-6-thio-5,7-diazaspiro[3,4]-5-octyl]-2-fluoro-3,5-dideutero-N-methylbenzamide |
| 55 | 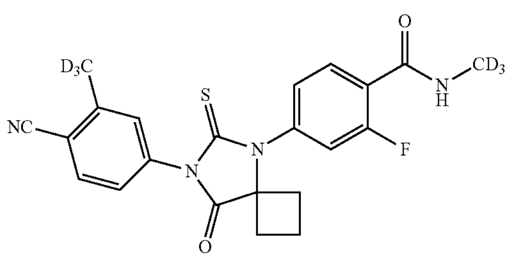 [SMILES: [2H]C([2H])([2H])NC(=O)c1ccc(N2C(=S)N(c3ccc(C#N)c(C([2H])([2H])[2H])c3)C(=O)C23CCC3)cc1F] | 4-[7-(2-trideuteromethyl-4-cyanophenyl)-8-oxo-6-thio-5,7-diazaspiro[3,4]-5-octyl]-2-fluoro-N-(trideuteromethyl)benzamide |
| 56 | 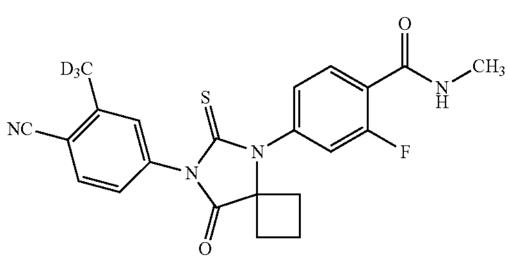 | 4-[7-(2-trideuteromethyl-4-cyanophenyl)-8-oxo-6-thio-5,7-diazaspiro[3,4]-5-octyl]-2-fluoro-N-methylbenzamide |
| 57 | 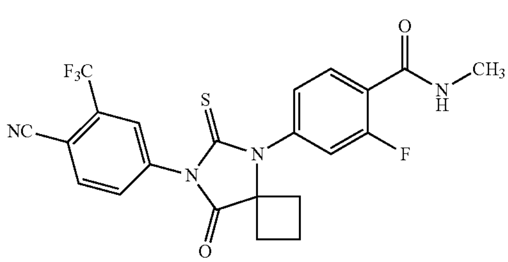 [SMILES: CNC(=O)c1ccc(N2C(=S)N(c3ccc(C#N)c(C(F)(F)F)c3)C(=O)C23CCC3)cc1F] | 4-[7-(2-trifluoromethyl-4-cyanophenyl)-8-oxo-6-thio-5,7-diazaspiro[3,4]-5-octyl]-2-dideutero-N-methylbenzamide |

TABLE 1-continued

| No. | structure | Name |
|---|---|---|
| 58 | 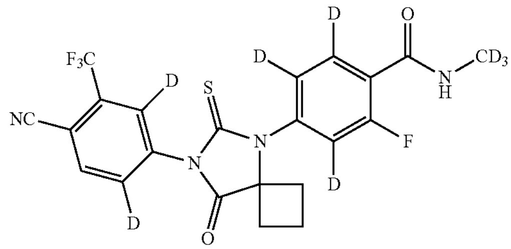 [SMILES: [2H]c1cc(C#N)c(C(F)(F)F)c([2H])c1N1C(=O)C2(CCC2)N(c2c([2H])c([2H])c(C(=O)NC([2H])([2H])[2H])c(F)c2[2H])C1=S] | 4-[7-(2-trifluoromethyl-4-cyano-2,6-dideuterophenyl)-8-oxo-6-thio-5,7-diazaspiro[3,4]-5-octyl]-2-fluoro-3,5,6-trideutero-N-(trideuteromethyl)benzamide |
| 59 | 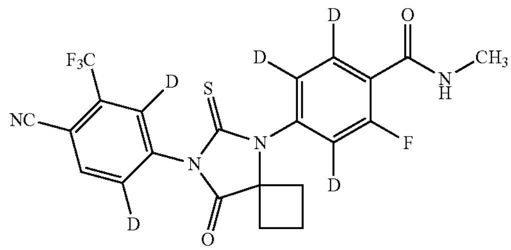 | 4-[7-(2-trifluoromethyl-4-cyano-2,6-dideuterophenyl)-8-oxo-6-thio-5,7-diazaspiro[3,4]-5-octyl]-2-fluoro-3,5,6-trideutero-N-methylbenzamide |
| 60 | 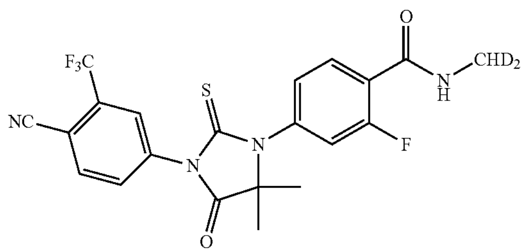 | 4-[7-[4-cyano-3-(trifluoromethyl)phenyl]-5,5-dimethyl-4-oxo-2-thio-1-imidazolidinyl]-2-fluoro-N-(dideuteromethyl)benzamide |
| 61 | 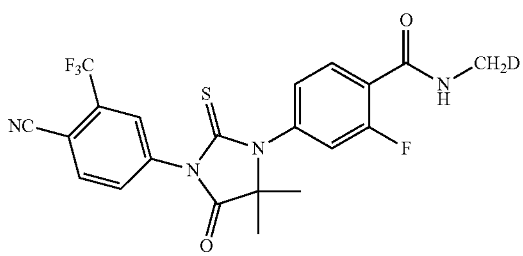 | 4-[7-[4-cyano-3-(trifluoromethyl)phenyl]-5,5-dimethyl-4-oxo-2-thio-1-imidazolidinyl]-2-fluoro-N-(deuteromethyl)benzamide |
| 62 | 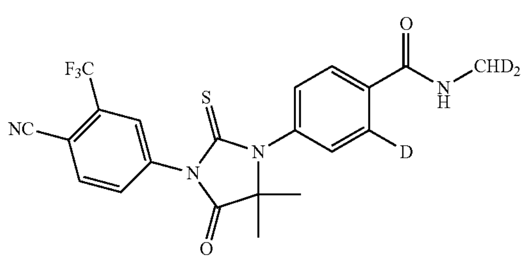 | 4-[7-[4-cyano-3-trifluoromethyl-2,6-phenyl]-5,5-dimethyl-4-oxo-2-thio-1-imidazolidinyl]-2-deutero-N-(dideuteromethyl)benzamide |
| 63 | 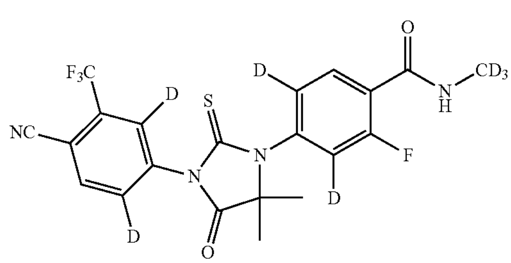 [SMILES: [2H]c1cc(C#N)c(C(F)(F)F)c([2H])c1N1C(=O)C(C)(C)N(c2c([2H])cc(C(=O)NC([2H])([2H])[2H])c(F)c2[2H])C1=S] | 4-[7-(4-cyano-3-trifluoromethyl-2,6-dideuterophenyl)-5,5-dimethyl-4-oxo-2-thio-1-imidazolidinyl]-2-fluoro-3,5-dideutero-N-(trideuteromethyl)benzamide |

TABLE 1-continued

| No. | structure | Name |
|---|---|---|
| 64 | 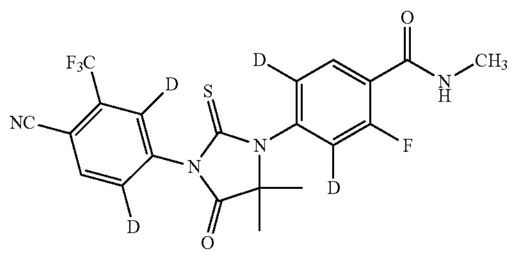 | 4-[7-(4-cyano-3-trifluoromethyl-2,6-dideuterophenyl)-5,5-dimethyl-4-oxo-2-thio-1-imidazolidinyl]-2-fluoro-3,5-dideutero-N-methylbenzamide |
| 65 | 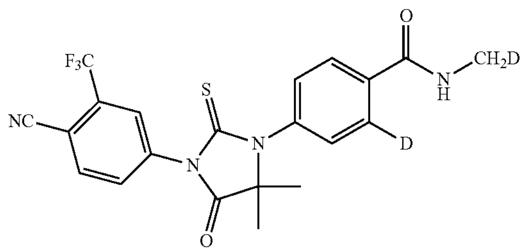 | 4-[7-(4-cyano-3-trifluoromethylphenyl)-5,5-dimethyl-4-oxo-2-thio-1-imidazolidinyl]-2-deutero-N-(deuteromethyl)benzamide |
| 66 | 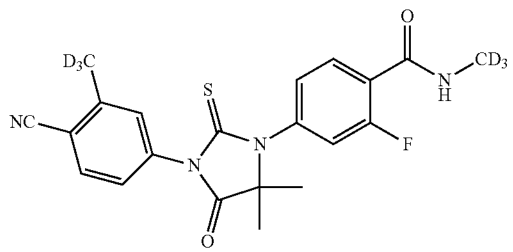 [SMILES: [2H]C([2H])([2H])NC(=O)c1ccc(N2C(=S)N(c3ccc(C#N)c(C([2H])([2H])[2H])c3)C(=O)C2(C)C)cc1F] | 4-[7-(4-cyano-3-(trideuteromethyl)phenyl]-5,5-dimethyl-4-oxo-2-thio-1-imidazolidinyl]-2-fluoro-N-(trideuteromethyl)benzamide |
| 67 | 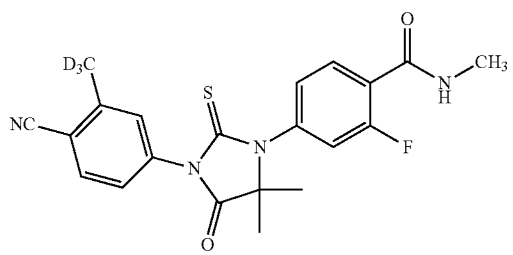 | 4-[7-(4-cyano-3-(trideuteromethyl)phenyl]-5,5-dimethyl-4-oxo-2-thio-1-imidazolidinyl]-2-fluoro-N-methylbenzamide |

Example 16

In Vitro Activity Test

The ability of compounds to inhibit the growth of prostate cancer cells was tested:

First, the human prostate cancer LNCaP (purchased from ATCC, USA) and 22RV1 (purchased from SIBS) cells were transferred to a RPMI1640 culture medium containing 10% charcoal-stripped fetal bovine serum (FBS). After cultured for three days, the cells were digested with 0.25% trypsin and counted through trypan blue staining. The cells were plated, with 100 μL cell suspension containing 5000 cells per well. 200 μL medium was added to the wells around the cell plate for avoiding edge effects.

The next day, 6 drug concentrations was prepared (48.6 μM, 19.44 μM, 7.776 μM, 3.11 μM, 1.24 μM, 0.5 μM) before administration, and 100 μl, of corresponding compound at corresponding concentration was added into each well of a cell plate. The cell plate was placed in a cell incubator for 30 min, 10 μL of 4 nM R1881 was added into each well and homogeneously mixed. Upon the addition of R1881, the cell plate was placed in a cell incubator and incubated at 37° C., under 5% $CO_2$ for 96 hours. Afterwards, 40 μL of MTT (prepared in PBS, concentration is 2.5 mg/mL) was added into each wells, and incubated at 37° C. for 2 hours. The supernatant was sucked off, and 100 μL of DMSO was added into each well. The plate was shaken by a vibrator for 10 min for dissolving formazan. The plate was read at 570 nm wavelength using a microplate reader in the unit of OD. The inhibition rate of test compounds was calculated with the following equation:

$$IR(\%) = (OD_{control} - OD_{sample})/(OD_{control} - OD_{blank}) \times 100\%$$

The inhibition rate curve of test compounds was plotted using the software XLFit (Formula 205), which can calculate the 50% inhibition rate, i.e. $IC_{50}$.

The results were shown in Table 2. The results demonstrated that, compared with bicalutamide, control compound 1 or 2, the compounds of the present invention exhibited better inhibition on the growth of prostate cancer cell, and for some compounds, the inhibition thereof were significantly increased.

TABLE 2

|  | LNCaP (IC$_{50}$, uM) | 22RV1 (IC$_{50}$, uM) |
| --- | --- | --- |
| bicalutamide | 18.45 | 30.88 |
| Example 1 (control compound 1, i.e. compound 7) | 4.09 | 25.99 |
| Example 4 (control compound 2, i.e. compound 17) | 8.93 | 30.56 |
| Example 2 (compound 11) | 1.37 | 20.76 |
| Example 3 (compound 15) | 0.36 | 14.96 |
| Example 5 (compound 19) | 2.07 | 23.37 |
| Example 6 (compound 21) | 0.99 | 13.43 |
| Example 7 (compound 24) | 2.20 | 19.72 |
| Example 13 (compound 44) | 2.74 | 15.55 |
| Example 9 (compound 29) | 1.86 | 26.51 |
| Example 11 (compound 36) | 1.75 | 18.93 |
| Example 8 (compound 27) | 1.01 | 18.69 |
| Example 14 (compound 45) | 1.50 | 26.92 |
| Example 10 (compound 31) | 1.49 | 26.71 |
| Example 12 (compound 41) | 2.42 | 25.82 |

Example 17

Activity Test In Vitro

The in vitro biological activity of test compounds of the present invention as androgen receptor antagonist can be tested by the methods as reported in J. Medcinal Chemistry (2010, page 2779-2796 and WO201 1/029392).

The inhibition activity of these compounds on prostate specific antigen (PSA) was determined using prostate cancer cells (LNCaP and 22RV1). Prostate cancer cells (LNCaP and 22RV1) could be purchased from ATCC, USA. The expression of PSA in cells was induced with the artificially synthesized androgen R1881 (methyltrienolone, androgen receptor activator) to increase the sensitivity of inhibition experiment. 50% inhibition concentration (IC$_{50}$) of the compounds on prostate specific antigen (PSA) in prostate cancer cells (LNCaP and 22RV1) was calculated according to reported methods. The results are shown in Table 3.

TABLE 3

| Example | LNCaP (IC$_{50}$, nM) | 22RV1 (IC$_{50}$, nM) |
| --- | --- | --- |
| Example 1 (control compound 1) | <1000 | <2000 |
| Example 4 (control compound 2) | <1000 | <2000 |
| Example 2 (compound 11) | <800 | <1600 |
| Example 3 (compound 15) | <400 | <1000 |
| Example 5 (compound 19) | <800 | <1600 |
| Example 6 (compound 21) | <400 | <1000 |
| Example 7 (compound 24) | <600 | <1000 |
| Example 8 (compound 27) | <600 | <1000 |

The results showed that, compared with control compounds, the compounds of formula I of the present invention could significantly inhibit prostate specific antigen (PSA).

Example 18

Pharmacokinetic Evaluation in Mice 10 mg/kg AF-484 (Example 6, compound 21) and AF-486 (Example 4, compound 17) were intragastrically administered to Healthy Kunming mice (KM mice), male, weighing 18-20 g. Compounds were dissolved in DMSO:PEG400:H$_2$O 1:5:14. The volume of administration was 10 mL/kg. Before testing, the mice fasted for 12 h and drunk water ad libitum. Then, the mice were fed together at 2 h after administration. 0.3 mL of blood were took from 3 mice through retrobulbar venous plexus at 0.5, 1.0, 2.0, 4.0, 6.0 and 24 h after administration, placed in heparinized tubes, and centrifuged for 5 min at 11000 rpm. The plasma was separated and frozen in a refrigerator at −20° C. 100 uL of serum was transferred with a pipettor into a clean plastic centrifuge tube marked with compound's name and time point, and diluted with acetonitrile (CH$_3$CN) and centrifuged. The concentration of drug was analyzed by LC-MS. Serum was stored at −80° C. before analysis.

The pharmacokinetic parameters of deuterated compound (Example 6, compound 21) and undeuterated compound (Example 4, compound 17) were show in following table. The experimental results showed that, compared with corresponding undeuterated compound 17, Cmax and AUC of the deuterated compound 21 of the present invention were significantly increased, in which Cmax was increased by at least 20%.

TABLE 4

| compound | Tmax (h) | Cmax (µg/mL) |
| --- | --- | --- |
| 21 | 6.0 | 10.4 |
| 17 | 6.0 | 8.45 |

Example 19

Pharmaceutical Compositions

| | |
| --- | --- |
| Compound 21 (Example 6) | 20 g |
| Starch | 140 g |
| Microcrystalline cellulose | 60 g |

The above materials were mixed by conventional methods and then packaged into ordinary gelatin capsules to obtain 1,000 capsules.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What is claimed is:

1. An imidazolidinedione compound of formula (I):

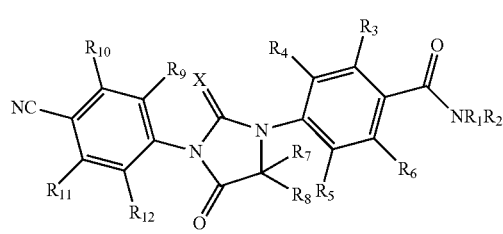

wherein,

R$^1$ is selected from hydrogen, deuterium, methyl and one or more deuterium-substituted or perdeuterated C$_1$-C$_4$ alkyl;

R² is selected from deuterium and one or more deuterium-substituted or perdeuterated C₁-C₄ alkyl;

wherein the deuterium content of R² is greater than the natural abundance of deuterium R³ is hydrogen, deuterium or halogen;

R⁴, R⁵, R⁶, R⁹, R¹⁰, R¹² are independently hydrogen, deuterium or halogen;

R⁷ and R⁸ are independently selected from methyl and one or more deuterium-substituted or perdeuterated C₁-C₄ alkyl, or R⁷ and R⁸ are joined to form C₃-C₆ cycloalkyl;

R¹¹ is non-deuterated, one or more deuterium-substituted or perdeuterated C₁-C₄ alkyl, or partly or totally halogen-substituted C₁-C₄ alkyl; and X is S or O;

or a crystal form, a pharmaceutically acceptable salt, or a hydrate thereof.

2. The compound of claim 1, wherein R¹ is selected from hydrogen, deuterated methyl, and deuterated ethyl; and R² is selected from deuterated methyl and deuterated ethyl.

3. The compound of claim 1, wherein when R¹ is hydrogen, R² is selected from the group consisting of mono-deuterated methyl, bi-deuterated methyl, tri-deuterated methyl, mono-deuterated ethyl, bi-deuterated ethyl, tri-deuterated ethyl, tetra-deuterated ethyl, and penta-deuterated ethyl.

4. The compound of claim 1, wherein when R¹ is hydrogen, R² is tri-deuterated methyl.

5. The compound of claim 1, wherein the compound is selected from the group consisting of -continued

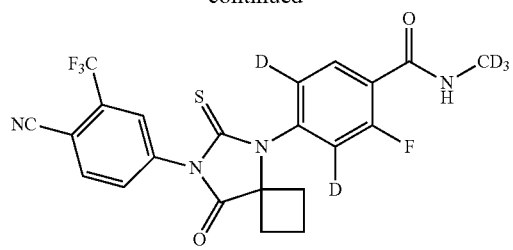

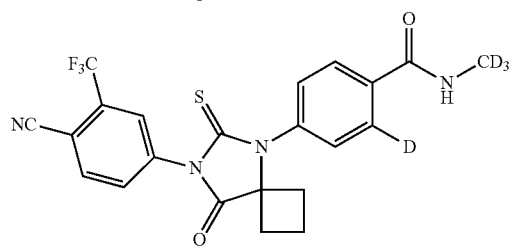

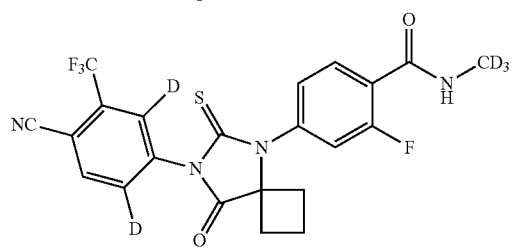

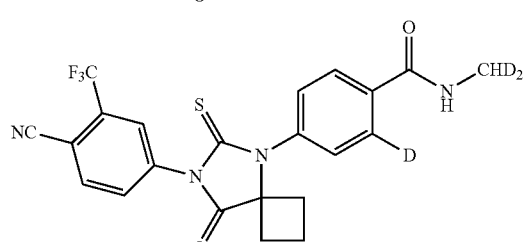

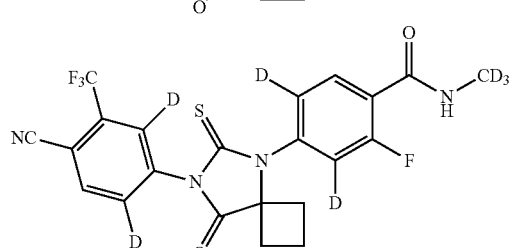

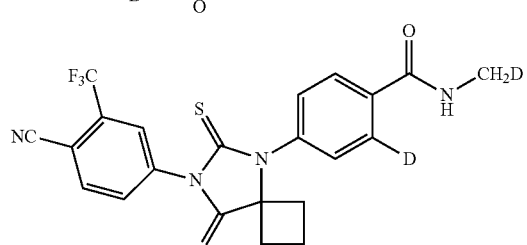

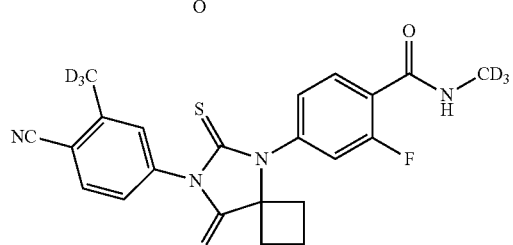

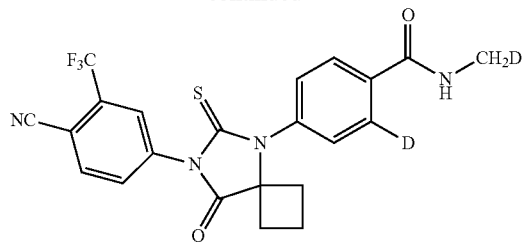
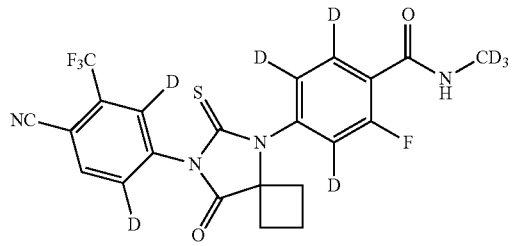
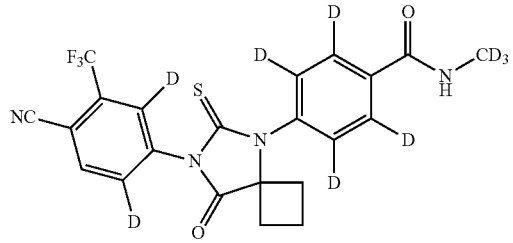
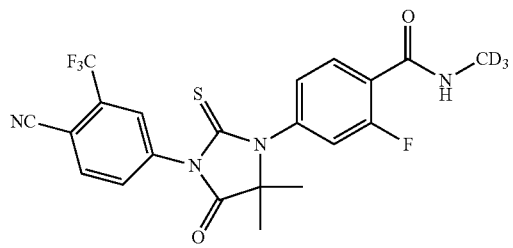
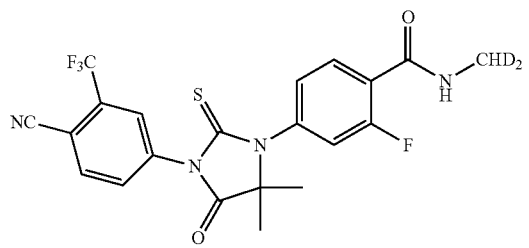
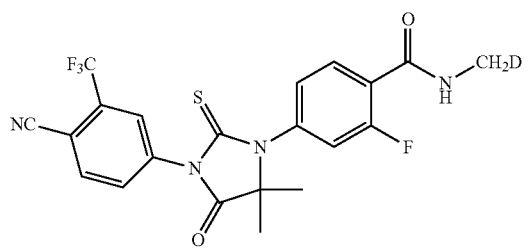
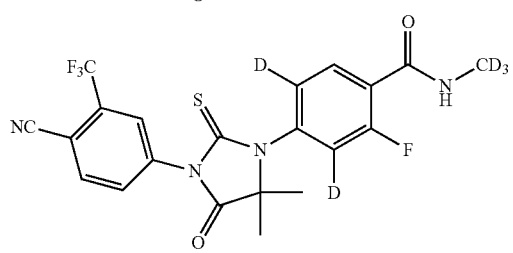
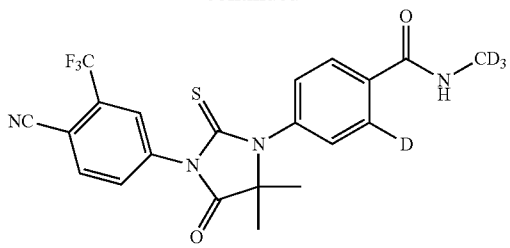
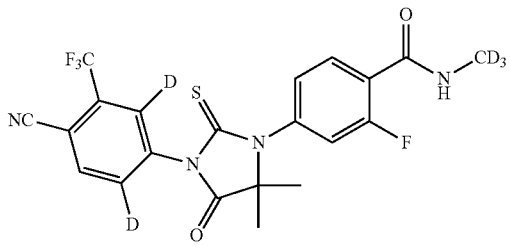
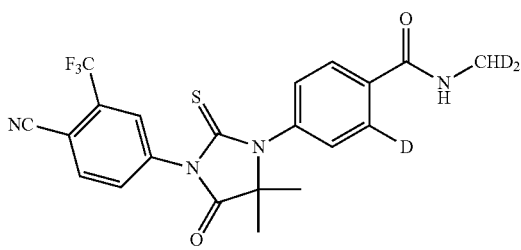
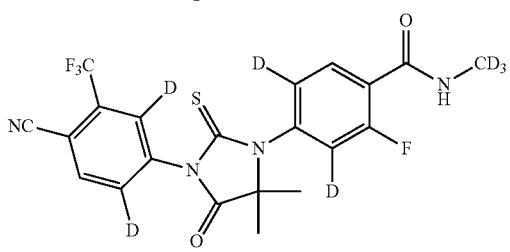
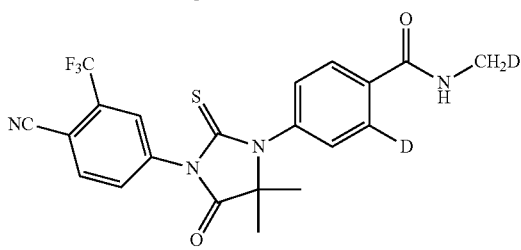
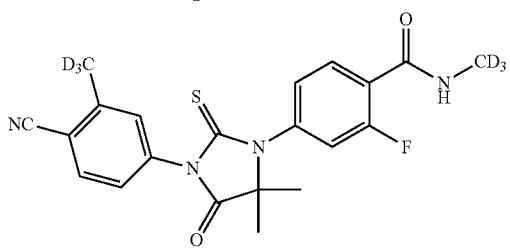
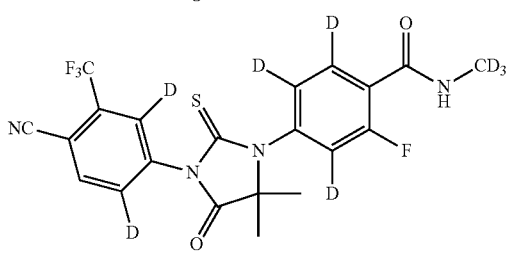

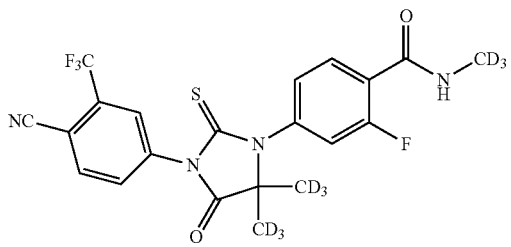

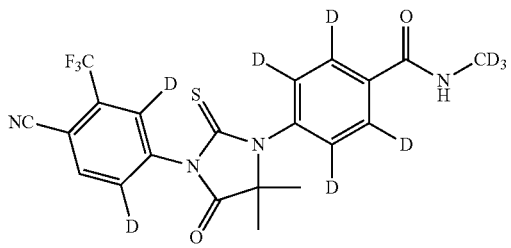

and

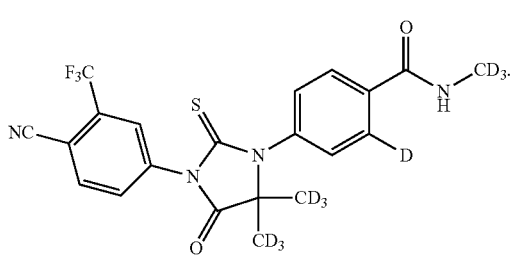

6. The compound of claim 1, wherein the compound is selected from the group consisting of

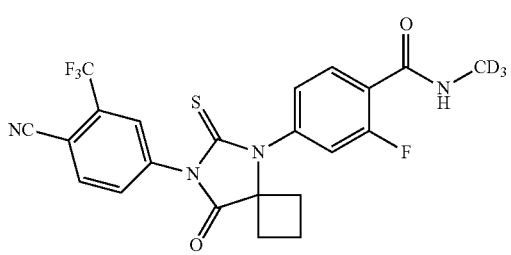

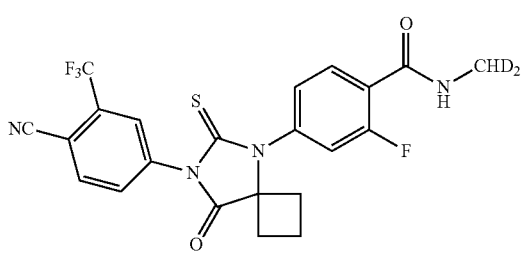

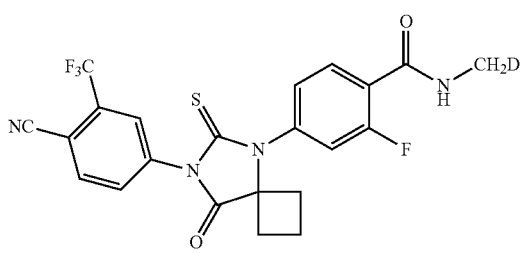

and

7. A method for preparing a pharmaceutical composition, comprising mixing the compound of claim 1, a crystal form, a pharmaceutically acceptable salt, or a hydrate thereof and a pharmaceutically acceptable carrier to form a pharmaceutical composition.

8. A pharmaceutical composition, comprising (1) the compound of claim 1, a crystal form, a pharmaceutically acceptable salt, or a hydrate thereof, and (2) a pharmaceutically acceptable carrier.

9. The pharmaceutical composition of claim 8, wherein the composition further comprises a therapeutic agent; and wherein the therapeutic agent is the therapeutic agent for treating alopecia, hair regeneration, pimples, acne or prostate cancer.

10. A method for treating disease, the method comprising:
administrating a compound of claim 1 or a pharmaceutically acceptable salt thereof as an androgen receptor antagonist to a subject with the disease;
wherein the disease is selected from the group consisting of alopecia, acne and prostate cancer.

11. The method of claim 10, wherein the disease is prostate cancer.

12. A method for treating a disease, the method comprising:
administering the pharmaceutical composition of claim 8 to a subject with the disease;
wherein the disease is selected from the group consisting of alopecia, acne and prostate cancer.

13. A method for preparing the compound of formula (I) of claim 1, comprising:
(1) in an acidic solvent, in the presence of cyanide, reacting compound 5a with $R_7C(O)R_8$, to form compound 6a,

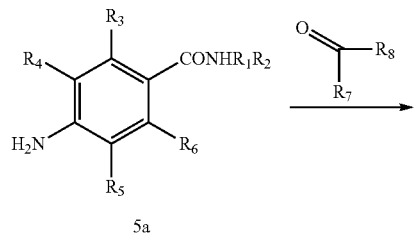

5a

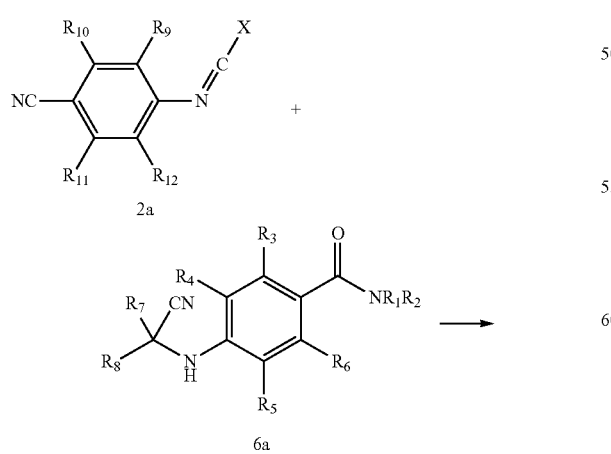

6a wherein the cyanide is TMSCN, sodium cyanide or potassium cyanide; and
(2) in an aprotic solvent, under an acidic condition, reacting compound 2a with compound 6a to form the compound of formula (I),

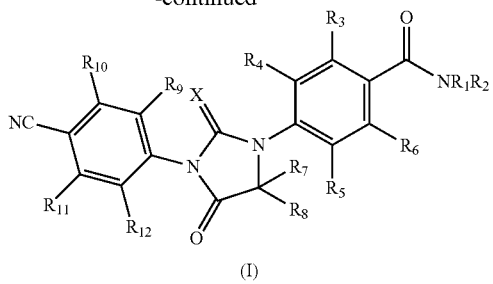

(I)

wherein $R^1$, $R^2$, $R^3$, $R^4$, $R^5$, $R^6$, $R^7$, $R^8$, $R^9$, $R^{10}$, $R^{11}$, $R^{12}$ and X are defined as those in claim 1.

14. The method of claim 13, wherein the method further comprises the following steps prior to step (1):
(1-1) in an inert solvent, reacting compound 3a with $NHR_1R_2$, to form compound 4a, and

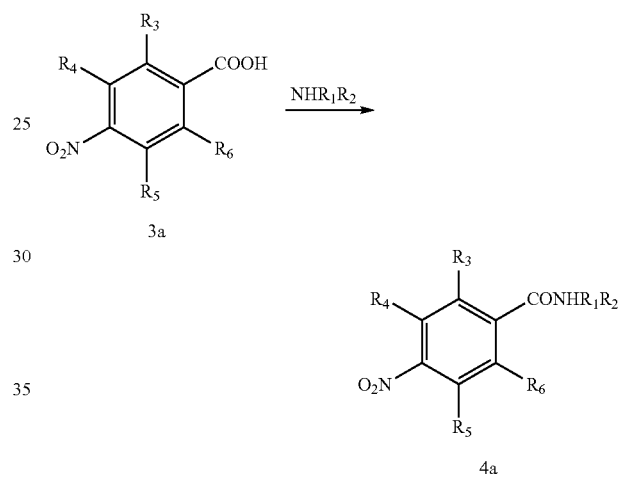

(1-2) in an inert solvent, in the presence of a reducing agent, reducing compound 4a to compound 5a,

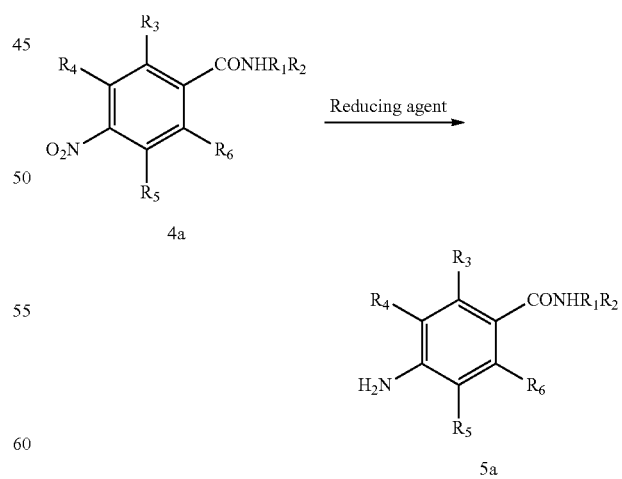

wherein $R^1$, $R^2$, $R^3$, $R^4$, $R^5$, and $R^6$ are defined as those-in claim 13.

* * * * *